(12) United States Patent
Stowell et al.

(10) Patent No.: US 10,233,222 B2
(45) Date of Patent: Mar. 19, 2019

(54) METHODS, COMPOSITIONS, DIAGNOSTICS AND ASSAYS FOR THE TREATMENT OF ALZHEIMER'S DISEASE

(71) Applicants: THE REGENTS OF THE UNIVERSITY OF COLORADO, A BODY CORPORATE, Denver, CO (US); AMIDEBIO, LLC, Boulder, CO (US)

(72) Inventors: Michael H. B. Stowell, Boulder, CO (US); Mikhail Plam, Boulder, CO (US)

(73) Assignees: THE REGENTS OF THE UNIVERSITY OF COLORADO, A BODY CORPORATE, Denver, CO (US); AMIDEBIO, LLC, Louisville, CO (US)

( * ) Notice: Subject to any disclaimer, the term of this patent is extended or adjusted under 35 U.S.C. 154(b) by 0 days.

(21) Appl. No.: 15/300,974

(22) PCT Filed: Apr. 2, 2015

(86) PCT No.: PCT/US2015/024175
§ 371 (c)(1),
(2) Date: Sep. 30, 2016

(87) PCT Pub. No.: WO2015/171229
PCT Pub. Date: Nov. 12, 2015

(65) Prior Publication Data
US 2017/0183388 A1 Jun. 29, 2017

Related U.S. Application Data

(60) Provisional application No. 61/974,320, filed on Apr. 2, 2014.

(51) Int. Cl.
*C07K 14/47* (2006.01)
*A61K 38/00* (2006.01)
*C07K 14/475* (2006.01)
*G01N 33/50* (2006.01)
*G01N 33/68* (2006.01)

(52) U.S. Cl.
CPC ........ *C07K 14/475* (2013.01); *C07K 14/4703* (2013.01); *C07K 14/4711* (2013.01); *G01N 33/5008* (2013.01); *G01N 33/6896* (2013.01); *A61K 38/00* (2013.01); *G01N 2500/02* (2013.01); *G01N 2800/2821* (2013.01)

(58) Field of Classification Search
CPC ...... C07K 14/475; A61K 38/00; A61K 38/04; A61K 38/08; A61K 38/10; A61K 38/185; G01N 33/5008; G01N 33/6896; G01N 2500/02; G01N 2800/2821
See application file for complete search history.

(56) References Cited

U.S. PATENT DOCUMENTS

| | | |
|---|---|---|
| 2002/0161607 A1 | 10/2002 | Subich |
| 2004/0175773 A1 | 9/2004 | Amson et al. |
| 2005/0079503 A1 | 4/2005 | Bowtell et al. |
| 2010/0029572 A1 | 2/2010 | Mossler et al. |
| 2011/0112990 A1 | 5/2011 | Stowell et al. |
| 2011/0160141 A1* | 6/2011 | Mossler ............... C07K 5/1008 514/17.8 |

FOREIGN PATENT DOCUMENTS

| WO | WO-2006103116 A1 | 10/2006 |
| WO | WO-2015171229 A1 | 11/2015 |

OTHER PUBLICATIONS

Gordon SL et al. Synaptophysin is required for synaptobrevin retrieval during synaptic vesicle endocytosis. J. Neuroscience, 2011, 31(39):14032-14036.*
Blanchard J et al. Rescue of synaptic failure and alleviation of learning and memory impairments in a trisomic mouse model of Down syndrome. J. Neuropathol. Exp. Neurol. 70(12):1070-1079. (Year: 2011).*
International Search Report and Written Opinion dated Aug. 21, 2015 for Internation Application No. PCT/US2015/024175.
Russell et al., Amyloid-b Acts as a Regulator of Neurotransmitter Release Disrupting the Interaction between Synaptophysin and VAMP2, PLOS ONE, (2012), 7(8): e43201 (14 pages).
Washbourne et al., Vesicle-associated membrane protein-2 (synaptobrevin-2) forms a complex with synaptophysin, Biochem. J., (1995) 305: 721-724.
Wheeler et al., Regulation of Synaptophysin Degradation by Mammalian Homologues of Seven in Absentia, J. Biol. Chem., (2002) 277: 10273-10282.

* cited by examiner

*Primary Examiner* — Kimberly Ballard
(74) *Attorney, Agent, or Firm* — Wilson Sonsini Goodrich & Rosati

(57) ABSTRACT

The invention provides compounds for the treatment of Alzheimer's disease, methods for the use of such compounds, assays for the identification of such compounds, and methods for diagnosis of Alzheimer's disease and diagnostic kits. Methods of marketing compounds are also disclosed. In one aspect, the disclosure provides a compound for the diagnosis or treatment of Alzheimer's disease wherein the compound is a modulator that inhibits the disruption by amyloid β of a complex comprising synaptophysin and/or synaptobrevin. In another aspect, the disclosure provides a pharmaceutical composition comprising the compounds disclosed herein in an amount sufficient to treat Alzheimer's disease in a subject. In another aspect, the disclosure provides a diagnostic composition comprising the compound disclosed herein.

11 Claims, 20 Drawing Sheets
Specification includes a Sequence Listing.

Human Ciliary Neurotrophic Factor Protein Sequence (SEQ ID NO:21):
MAFTEHSPLTPHRRDLCSRSIWLARKIRSDLTALTESYVKHQGLNKNINLDSADGMPVASTDQWSEL
TEAERLQENLQAYRTFHVLLARLLEDQQVHFTPTEGDFHQAIHTLLLQVAAFAYQIEELMILLEYKIP
RNEADGMPINVGDGGLFEKKLWGLKVLQELSQWTVRSIHDLRFISSHQTGIPARGSHYIANNKKM

METHODS, COMPOSITIONS, DIAGNOSTICS AND ASSAYS FOR THE TREATMENT OF ALZHEIMER'S DISEASE

CROSS REFERENCE

This application is a U.S. National Phase Application under 35 U.S.C. § 371 of International Application No. PCT/US2015/024175, filed Apr. 2, 2015, which claims the benefit of U.S. Provisional Application No. 61/974,320, filed Apr. 2, 2014, each of which are incorporated herein by reference in their entireties.

REFERENCE TO A SEQUENCE LISTING SUBMITTED VIA EFS-WEB

The content of the ASCII text file of the sequence listing named "39538-703-601_SL.txt" which is 10 kb in size was created on Jun. 2, 2015, and electronically submitted via EFS-Web herewith the application is incorporated herein by reference in its entirety.

BACKGROUND OF THE INVENTION

Alzheimer's disease (AD) affects more than 35 million people worldwide and costs more than 170 billion dollars to treat and manage in the U.S. alone. AD is a slowly progressing disease characterized by the overproduction of amyloid beta (Aβ) peptide in neuronal tissue. While the exact mode of action of Aβ peptide is unclear, overproduction ultimately leads to neuron death and the clinical symptoms of AD. The complexity of AD and the significant public health issue it poses demands the exploration of a variety of novel strategies that hold promise for effective diagnosis and treatment.

Current treatments for AD treat the symptoms but do not treat the underlying disease, and have only modest effects on patient outcome. Current strategies to treat the disease have focused on relieving the amyloid burden through the inhibition of the gamma secretase complex or anti-amyloid antibodies. To date these strategies have failed to achieve significant improvements in patient outcome despite a number of large phase III clinical trials. Emerging therapeutic strategies include attempts to limit tau tangles as well as metabolic interventions. None of these strategies are focused on a direct molecular target of Aβ but rather downstream cellular effects of excess Aβ.

There remains a need to identify steps in the causation of the symptoms of Alzheimer's disease, to develop diagnostics to identify afflicted patients, and to develop therapeutic strategies to address them.

SUMMARY OF THE INVENTION

Various embodiments of the invention arise from the discovery that the synaptophysin/synaptobrevin complex is disrupted and/or prevented from properly assembling by amyloid β peptides. The disruption and/or improper assembly may result in the increased proteolytic degradation of synaptophysin.

In one aspect, the disclosure provides a compound for the diagnosis or treatment of Alzheimer's disease wherein the compound is a modulator that inhibits the disruption by amyloid β of a complex comprising synaptophysin and/or synaptobrevin. In some embodiments, the compound is an isolated and purified peptide having an amino acid sequence that is at least 50% homologous to a fragment of SEQ ID. NO: 21. In some embodiments, the compound is an isolated and purified peptide having an amino acid sequence that is at least 60%, 70%, 75%, 80%, 85%, 90%, 95%, or more homologous to a fragment of SEQ ID. NO: 21. In some embodiments, the fragment of SEQ ID. NO: 21 comprises 6 or more contiguous amino acids. In some embodiments, the modulator that inhibits the disruption by amyloid β of a complex comprising synaptophysin and/or synaptobrevin directly interacts with the complex. In some embodiments, the isolated and purified peptide comprises an amino acid sequence having at least 50% sequence homology to the amino acid sequence VGDGGLFEKKL (SEQ ID NO: 1). In some embodiments, the compound is an isolated and purified peptide having an amino acid sequence that is at least 60%, 70%, 75%, 80%, 85%, 90%, 95%, or more homologous to the amino acid sequence VGDGGLFEKKL (SEQ ID NO: 1). In some embodiments the peptide comprises an amino acid sequence $X_1X_2X_3X_4X_5X_6X_7X_8X_9X_{10}X_{11}$, wherein:

$X_1$ is valine or isoleucine;
$X_2$ is glycine;
$X_3$ is aspartic acid or glutamine;
$X_4$ is glycine;
$X_5$ is glycine, serine, or aspartic acid;
$X_6$ is leucine, methionine, aspartic acid, valine, arginine, glutamine, isoleucine, or threonine;
$X_7$ is phenylalanine, or isoleucine;
$X_8$ is glutamic acid, glutamine, threonine, or lysine;
$X_9$ is lysine, threonine, glutamine, arginine, or alanine;
$X_{10}$ is lysine, arginine or glutamic acid; and
$X_{11}$ is isoleucine, methionine, leucine, phenylalanine, lysine, tryptophan, tyrosine.

In some embodiments, the peptide comprises the amino acid sequence of SEQ ID NO: 1. In some embodiments, peptide comprises an amino acid sequence selected from a group consisting of SEQ ID NO: 1-20.

In another aspect, the disclosure provides a pharmaceutical composition comprising the compounds disclosed herein in an amount sufficient to treat Alzheimer's disease in a subject. In some aspects, the pharmaceutical composition further comprises a pharmaceutically acceptable carrier.

In another aspect, the disclosure provides a diagnostic composition comprising the compound disclosed herein in an amount sufficient to diagnose Alzheimer's disease in a subject. In some aspects, the diagnostic composition further comprises a carrier compatible with a diagnostic assay.

In another aspect, the disclosure provides a compound for the diagnosis or treatment of Alzheimer's disease wherein the compound modulates a complex comprising synaptophysin and/or synaptobrevin; and wherein the compound is an isolated and purified peptide having an amino acid sequence that is at least 50% homologous to a fragment of SEQ ID. NO: 21. In some embodiments, the compound is an isolated and purified peptide having an amino acid sequence that is at least 60%, 70%, 75%, 80%, 85%, 90%, 95%, or more homologous to a fragment of SEQ ID. NO: 21. In some embodiments, the fragment of SEQ ID. NO: 21 comprises 6 or more contiguous amino acids. In some embodiments, the modulation comprises stabilization of the complex. In some embodiments, the modulation comprises inhibition of a disruptor of the complex. In some embodiments, the disruptor is amyloid β. In some embodiments, the compound binds to amyloid β. In some embodiments, the compound binds to the complex comprising synaptophysin and/or synaptobrevin.

In some embodiments, the peptide comprises an amino acid sequence having at least 50% sequence homology to the amino acid sequence VGDGGLFEKKL (SEQ ID NO: 1). In some embodiments, the compound is an isolated and purified peptide having an amino acid sequence that is at least 60%, 70%, 75%, 80%, 85%, 90%, 95%, or more homologous to the amino acid sequence VGDGGLFEKKL (SEQ ID NO: 1). In some embodiments, the peptide comprises an amino acid sequence $X_1X_2X_3X_4X_5X_6X_7X_8X_9X_{10}X_{11}$, wherein:

$X_1$ is valine or isoleucine;
$X_2$ is glycine;
$X_3$ is aspartic acid or glutamine;
$X_4$ is glycine;
$X_5$ is glycine, serine, or aspartic acid;
$X_6$ is leucine, methionine, aspartic acid, valine, arginine, glutamine, isoleucine, or threonine;
$X_7$ is phenylalanine, or isoleucine;
$X_8$ is glutamic acid, glutamine, threonine, or lysine;
$X_9$ is lysine, threonine, glutamine, arginine, or alanine;
$X_{10}$ is lysine, arginine or glutamic acid; and
$X_{11}$ is isoleucine, methionine, leucine, phenylalanine, lysine, tryptophan, tyrosine.

In some embodiments, the peptide is selected from a group consisting of SEQ ID NO: 1-SEQ ID NO: 20. In some embodiments, the peptide comprises the amino acid sequence of SEQ ID NO: 1.

In embodiments, the disclosure provides a pharmaceutical composition comprising the compound for the diagnosis or treatment of Alzheimer's disease wherein the compound modulates a complex comprising synaptophysin and/or synaptobrevin. In some embodiments, the pharmaceutical composition further comprises a pharmaceutically acceptable carrier. In some embodiments, the disclosure provides a diagnostic composition comprising the compound for the diagnosis or treatment of Alzheimer's disease wherein the compound modulates a complex comprising synaptophysin and/or synaptobrevin. In some aspect, the diagnostic composition further comprises a carrier acceptable for a diagnostic assay.

In another aspect, the disclosure provides a method for diagnosing Alzheimer's disease comprising adding a modulator to a biological sample from a potential candidate for Alzheimer's disease, and comparing level of complex comprising synaptophysin and/or synaptobrevin in the biological sample with level of complex in a control sample, wherein the modulator inhibits disruption of the complex by amyloid β.

In another aspect, the disclosure provides a method for diagnosing Alzheimer's disease comprising adding a modulator to a biological sample from a potential candidate for Alzheimer's disease and measuring amount of a complex comprising synaptophysin and/or synaptobrevin, wherein the modulator inhibits action of amyloid β on the complex comprising synaptophysin and/or synaptobrevin. In some embodiments, the pharmaceutical composition further comprises a pharmaceutically acceptable carrier.

In another aspect the disclosure provides a method for treating Alzheimer's disease, the method comprising administering to a subject in need thereof a pharmaceutical composition comprising a modulator that inhibits disruption of a complex by amyloid β in an amount sufficient to treat Alzheimer's disease, wherein the complex comprises synaptophysin and/or synaptobrevin.

In some embodiments, the modulator in the methods described herein directly interacts with the complex. In some embodiments, the modulator in the methods described herein is selected from the group consisting of: small molecules, organic compounds, inorganic compounds, nucleic acids, peptides, peptide mimetics, proteins, antibodies, and antibody fragments. In some embodiments, the modulator is a peptide. In some embodiments, the peptide has an amino acid sequence that is at least 50% homologous to a fragment of SEQ ID. NO: 21. In some embodiments, the compound is an isolated and purified peptide having an amino acid sequence that is at least 60%, 70%, 75%, 80%, 85%, 90%, 95%, or more homologous to a fragment of SEQ ID. NO: 21. In some embodiments, the fragment of SEQ. ID NO: 21 comprises 6 or more amino acids. In some embodiments, the peptide comprises 6 or more contiguous amino acids selected from SEQ ID NO: 21. In some embodiments, the peptide comprises an amino acid sequence having at least 50% sequence homology to the amino acid sequence VGDGGLFEKKL (SEQ ID NO: 1). In some embodiments, the compound is an isolated and purified peptide having an amino acid sequence that is at least 60%, 70%, 75%, 80%, 85%, 90%, 95%, or more homologous to the amino acid sequence VGDGGLFEKKL (SEQ ID NO: 1). In some embodiments, the peptide comprises an amino acid sequence $X_1X_2X_3X_4X_5X_6X_7X_8X_9X_{10}X_{11}$, wherein:

$X_1$ is valine or isoleucine;
$X_2$ is glycine;
$X_3$ is aspartic acid or glutamine;
$X_4$ is glycine;
$X_5$ is glycine, serine, or aspartic acid;
$X_6$ is leucine, methionine, aspartic acid, valine, arginine, glutamine, isoleucine, or threonine;
$X_7$ is phenylalanine, or isoleucine;
$X_8$ is glutamic acid, glutamine, threonine, or lysine;
$X_9$ is lysine, threonine, glutamine, arginine, or alanine;
$X_{10}$ is lysine, arginine or glutamic acid; and
$X_{11}$ is isoleucine, methionine, leucine, phenylalanine, lysine, tryptophan, tyrosine.

In some embodiments, the peptide comprises an amino acid sequence selected from the group consisting of SEQ ID NOs: 1-20. In some embodiments, the peptide comprises the amino acid sequence of SEQ ID NO: 1.

In another aspect, the disclosure provides a method for treating Alzheimer's disease comprising administering to a subject in need thereof a pharmaceutical composition comprising a modulator that modulates a complex comprising synaptophysin and/or synaptobrevin in an amount sufficient to treat Alzheimer's disease. In some embodiments, the pharmaceutical composition further comprises a pharmaceutically acceptable carrier. In some embodiments, the modulation comprises stabilization of the complex. In some embodiments, the modulation comprises inhibition of a disruptor of the complex. In some embodiments, the disruptor is amyloid β. In some embodiments, the modulator interacts with the amyloid β. In some embodiments, the modulator binds to the complex comprising synaptophysin and/or synaptobrevin. In some embodiments, the modulator is selected from the group consisting of: small molecules, organic compounds, inorganic compounds, nucleic acids, peptides, peptide mimetics, proteins, antibodies, and antibody fragments. In some embodiments, the modulator is a peptide. In some embodiments, the peptide has an amino acid sequence that is at least 50% homologous to a fragment of SEQ ID. NO: 21. In some embodiments, the compound is an isolated and purified peptide having an amino acid sequence that is at least 60%, 70%, 75%, 80%, 85%, 90%, 95%, or more homologous to a fragment of SEQ ID. NO: 21. In some embodiments, the fragment of SEQ. ID NO: 21 comprises 6 or more amino acids. In some embodiments, the peptide comprises 6 or more contiguous amino acids selected from SEQ ID NO: 21. In some embodiments, the peptide comprises an amino acid sequence having at least 50% sequence homology to the amino acid sequence VGDGGLFEKKL (SEQ ID NO: 1). In some embodiments, the compound is an isolated and purified peptide having an amino acid sequence that is at least 60%, 70%, 75%, 80%, 85%, 90%, 95%, or more homologous to the amino acid sequence VGDGGLFEKKL (SEQ ID NO: 1). In some embodiments, the peptide comprises an amino acid sequence $X_1X_2X_3X_4X_5X_6X_7X_8X_9X_{10}X_{11}$, wherein:

$X_1$ is valine or isoleucine;
$X_2$ is glycine;
$X_3$ is aspartic acid or glutamine;
$X_4$ is glycine;
$X_5$ is glycine, serine, or aspartic acid;
$X_6$ is leucine, methionine, aspartic acid, valine, arginine, glutamine, isoleucine, or threonine;
$X_7$ is phenylalanine, or isoleucine;
$X_8$ is glutamic acid, glutamine, threonine, or lysine;
$X_9$ is lysine, threonine, glutamine, arginine, or alanine;
$X_{10}$ is lysine, arginine or glutamic acid; and
$X_{11}$ is isoleucine, methionine, leucine, phenylalanine, lysine, tryptophan, tyrosine.

In some embodiments, the peptide comprises an amino acid sequence selected from the group consisting of SEQ ID NOs: 1-20. In some embodiments, the peptide comprises the amino acid sequence of SEQ ID NO: 1.

In another aspect, the disclosure provides an assay for the identification of compounds for treating Alzheimer's disease comprising the use of surface plasmon resonance (SPR), the assay comprising analyzing a test compound to determine a level of inhibition of Aβ42 binding to synaptophysin and/or synaptobrevin and identifying the test compound as a compound for the treatment of Alzheimer's disease based on the level of inhibition.

In another aspect, the disclosure provides an assay for the identification of compounds for treating Alzheimer's disease comprising contacting a cell with a test compound, determining a level of a complex comprising synaptophysin and/or synaptobrevin, and identifying the test compound as a compound for the treatment of Alzheimer's disease based on the level.

In another aspect, the disclosure provides an assay for the identification of compounds for treating Alzheimer's disease comprising contacting a cell with a test compound, determining a level of a complex comprising synaptophysin and/or synaptobrevin, and identifying the test compound as a compound for the treatment of Alzheimer's disease based on a level of inhibition of disruption of the complex by amyloid β.

In some embodiments, the cell comprises one or more recombinant proteins. In some embodiments, the cell is maintained in cell culture.

In some embodiments, the one or more recombinant proteins is selected from the group consisting of: synaptophysin, synaptobrevin, and amyloid β.

In some embodiments, the synaptophysin, the synaptobrevin, or both comprise a detectable label. In some embodiments, the label is a fluorescent label. In some embodiments, the level of the complex is measured by detection of fluorescence resonance energy transfer (FRET).

In some embodiments, the test compound is selected from the group consisting of: small molecules, organic compounds, inorganic compounds, nucleic acids, peptides, peptide mimetics, proteins, antibodies, and antibody fragments. In some embodiments, the compound comprises a modulator that inhibits the disruption by amyloid β of a complex comprising synaptophysin and/or synaptobrevin in an amount sufficient to treat Alzheimer's disease. In some embodiments, the modulator interacts directly with the complex.

In another aspect, the disclosure provides a method of evaluating the commercial market for a modulator that inhibits the disruption by amyloid β of a complex comprising synaptophysin and/or synaptobrevin comprising
a) identifying the modulator according to the assay;
b) making sample amounts of the modulator available for no cost or minimal cost; and
c) measuring the number of requests for the modulator over a period of time.

In some embodiments, the modulator is greater than 99% pure.

In another aspect, the disclosure provides a method of inhibiting synaptophysin degradation in vivo comprising administering to a patient in need thereof an exogenous substrate of SIAH-1/2 wherein SIAH-1/2 acts on the exogenous substrate. In some embodiments, the synaptophysin degradation is inhibited by an amount selected from greater than 10%, 20%, 30%, 40%, 50%, 60%, 70%, 80%, or 90%. In some embodiments, the exogenous substrate is a peptide. In some embodiments, the patient in need thereof has or is at risk of having Alzheimer's disease.

These and other embodiments are described herein.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 5 shows the amino acid sequence of human ciliary neurotrophic factor (SEQ ID NO:21).

DETAILED DESCRIPTION OF THE INVENTION

Definitions

Figure 1:
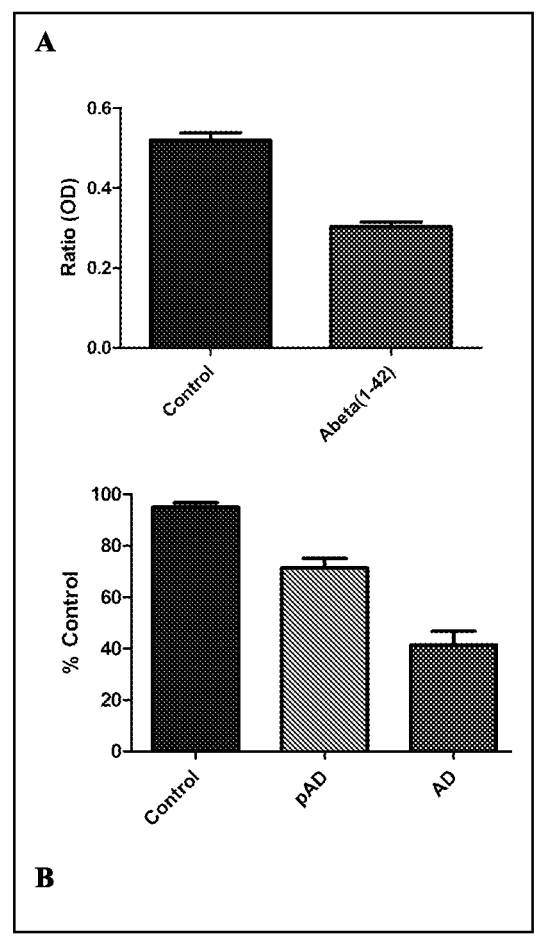
FIG. 1A shows the results of measurements of the level of Syp/Syb complex in cultured cells.
FIG. 1B shows the results of measurements of the level of Syp in cells from human subjects.

The terms "polypeptide", "peptide" and "protein" are used interchangeably herein to refer to polymers of amino acids of any length. The polymer may be linear or branched, it may comprise modified amino acids, and it may be interrupted by non amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" refers to either natural and/or unnatural or synthetic amino acids, including glycine and both the D or L optical isomers, and amino acid analogs and peptidomimetics.

The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof Polynucleotides may have any three dimensional structure, and may perform any function, known or unknown. The following are non limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non nucleotide components. A polynucleotide may be further modified after polymerization, such as by conjugation with a labeling component.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

As used herein, "treatment" or "treating," or "palliating" or "ameliorating" are used interchangeably. These terms refer to an approach for obtaining beneficial or desired results including but not limited to a therapeutic benefit and/or a prophylactic benefit. By therapeutic benefit is meant any therapeutically relevant improvement in or effect on one or more diseases, conditions, or symptoms under treatment. For prophylactic benefit, the compositions may be administered to a subject at risk of developing a particular disease, condition, or symptom, or to a subject reporting one or more of the physiological symptoms of a disease, even though the disease, condition, or symptom may not have yet been manifested.

As used herein, "diagnostic" refers to a biomarker or other assay for ascertaining stage of disease, severity, likelihood of developing, likelihood of benefiting from treatment, and the like with respect to Alzheimer's disease, and may include a "differential diagnosis" by which is meant the process by which a physician produces a diagnosis that explains a patient's symptoms. Typically, a "differential diagnosis" involves determining, from a set of possible candidates, which disease is causing the symptoms.

The term "effective amount" or "therapeutically effective amount" refers to the amount of an agent that is sufficient to effect beneficial or desired results. The therapeutically effective amount will vary depending upon the subject and disease condition being treated, the weight and age of the subject, the severity of the disease condition, gender, the manner of administration and the like, which can readily be determined by one of ordinary skill in the art. The term also applies to a dose that will provide an image for detection by any one of the imaging methods described herein. The specific dose will vary depending on the particular agent chosen, the dosing regimen to be followed, whether it is administered in combination with other compounds, timing of administration, the tissue to be imaged, and the physical delivery system in which it is carried.

The term "naturally occurring amino acid" refers to any one of the twenty amino acids commonly found in peptides synthesized in nature, and known by the one letter abbreviations A, R, N, C, D, Q, E, G, H, I, L, K, M, F, P, S, T, W, Y and V.

The following table shows a summary of the properties of natural amino acids:

| Amino Acid | 3-Letter Code | 1-Letter Code | Side-chain Polarity | Side-chain charge (pH 7.4) | Hydropathy Index |
|---|---|---|---|---|---|
| Alanine | Ala | A | nonpolar | neutral | 1.8 |
| Arginine | Arg | R | polar | positive | −4.5 |
| Asparagine | Asn | N | polar | neutral | −3.5 |
| Aspartic acid | Asp | D | polar | negative | −3.5 |
| Cysteine | Cys | C | polar | neutral | 2.5 |
| Glutamic acid | Glu | E | polar | negative | −3.5 |
| Glutamine | Gln | Q | polar | neutral | −3.5 |
| Glycine | Gly | G | nonpolar | neutral | −0.4 |
| Histidine | His | H | polar | positive(10%) neutral(90%) | −3.2 |
| Isoleucine | Ile | I | nonpolar | neutral | 4.5 |
| Leucine | Leu | L | nonpolar | neutral | 3.8 |
| Lysine | Lys | K | polar | positive | −3.9 |
| Methionine | Met | M | nonpolar | neutral | 1.9 |
| Phenylalanine | Phe | F | nonpolar | neutral | 2.8 |
| Proline | Pro | P | nonpolar | neutral | −1.6 |
| Serine | Ser | S | polar | neutral | −0.8 |
| Threonine | Thr | T | polar | neutral | −0.7 |
| Tryptophan | Trp | W | nonpolar | neutral | −0.9 |
| Tyrosine | Tyr | Y | polar | neutral | −1.3 |
| Valine | Val | V | nonpolar | neutral | 4.2 |

"Hydrophobic amino acids" include small hydrophobic amino acids and large hydrophobic amino acids. "Small hydrophobic amino acids" are glycine, alanine, proline, and analogs thereof "Large hydrophobic amino acids" are valine, leucine, isoleucine, phenylalanine, methionine, tryptophan, tyrosine, and analogs thereof "Polar amino acids" are serine, threonine, asparagine, glutamine, cysteine, and analogs thereof "Charged amino acids" include positively charged amino acids and negatively charged amino acids. "Positively charged amino acids" include lysine, arginine, histidine, and analogs thereof "Negatively charged amino acids" include aspartate, glutamate, and analogs thereof The term "amino acid analog" refers to a molecule which is structurally similar to an amino acid and which can be substituted for an amino acid in the formation of a peptide. Amino acid analogs include, without limitation, β-amino acids and amino acids where the amino or carboxy group is substituted by a similarly reactive group (e.g., substitution of the primary amine with a secondary or tertiary amine, or substitution of the carboxy group with an ester).

The term "non-natural amino acid" refers to an amino acid which is not one of the twenty amino acids commonly found in peptides synthesized in nature, and known by the one letter abbreviations A, R, N, C, D, Q, E, G, H, I, L, K, M, F, P, S, T, W, Y and V.

A "non-essential" amino acid residue is a residue that can be altered from the wild-type sequence of a polypeptide without abolishing or substantially abolishing its essential biological or biochemical activity (e.g., receptor binding or activation). An "essential" amino acid residue is a residue that, when altered from the wild-type sequence of the polypeptide, results in abolishing or substantially abolishing the polypeptide's essential biological or biochemical activity.

A "conservative amino acid substitution" is one in which the amino acid residue is replaced with an amino acid residue having a similar side chain. Families of amino acid residues having similar side chains have been defined in the art. These families include amino acids with basic side chains (e.g., K, R, H), acidic side chains (e.g., D, E), uncharged polar side chains (e.g., G, N, Q, S, T, Y, C), nonpolar side chains (e.g., A, V, L, I, P, F, M, W), beta-branched side chains (e.g., T, V, I) and aromatic side chains (e.g., Y, F, W, H). Thus, a predicted nonessential amino acid residue in a polypeptide, for example, is replaced with another amino acid residue from the same side chain family. Other examples of acceptable substitutions are substitutions based on isosteric considerations (e.g. norleucine for methionine) or other properties (e.g. 2-thienylalanine for phenylalanine).

Compounds

In one aspect, the invention provides a compound for the treatment of Alzheimer's disease (AD). In one embodiment, the compound modulates a complex comprising synaptophysin (Syp) and synaptobrevin (Syb). Modulation can be direct, such as through binding to the complex or chemically modifying the complex, or indirect, such as by interacting with an inhibitor or disruptor of the complex. Modulation can be positive or negative, such that activity level, amount, and/or stability of the complex is increased or decreased, respectively.

In some embodiments, the compound chemically modifies the Syp/Syb complex. Examples of chemical modifications include, but are not limited to glycosylation, phosphorylation, acetylation, methylation, biotinylation, glutamylation, glycylation, hydroxylation, isomerization, prenylation, myristoylation, lipoylation, phosphopantetheinylation, sulfation, ISGylation, nitrosylation, palmitoylation, SUMOylation, ubiquitination, neddylation, citrullination, amidation, and disulfide bond formation, disulfide bond reduction. Other possible chemical additions or modifications of biomolecules include the formation of protein carbonyls, direct modifications of protein side chains, such as o-tyrosine, chloro-, nitrotyrosine, and dityrosine, and protein adducts derived from reactions with carbohydrate and lipid derivatives. Other modifications may be non-covalent, such as binding of a ligand or binding of an allosteric modulator. Modifications may be made to one or more members of the Syp/Syb complex, including but not limited to synaptophysin and/or synaptobrevin.

In some embodiments, the modulator interacts directly with the Syp/Syb complex, such as by binding. Examples of binding forces by which the modulator may interact with the complex include but are not limited to covalent bonds, dipole interactions, electrostatic forces, hydrogen bonds, hydrophobic interactions, ionic bonds, and van der Waals forces. One or more members of the complex may participate in binding the modulator, including but not limited to Syp and/or Syb. In some embodiments, binding of the modulator induces a conformational change in one or more members of the Syp/Syb complex, including but not limited to Syp and/or Syb. In some embodiments, binding of the modulator sterically hinders an interaction between the Syp/Syb complex and another molecule, such as by blocking a binding site or a site of chemical modification.

In some embodiments, the modulator inhibits the activity of a disruptor of the Syp/Syb complex. In general, a disruptor is any agent that negatively regulates one or more functions of the Syp/Syb complex. Negative regulation includes degradation of one or more members of the complex, disruption of an interaction between one or more members of the complex, reducing an activity of the complex, reducing an expression level of one or more members of the complex, reducing the stability of the complex, and/or reducing the amount of one or more members of the complex. Inhibition of disruptor activity may be direct or indirect with respect to the complex or the disruptor. For example, interaction between a disruptor and the complex may be reduced by a modulator binding to or chemically modifying the complex. As a further example, interaction between a disruptor and the complex may be reduced by a modulator that binds to, chemically modifies, reduces expression level of, reduces stability of, reduces the amount of, degrades, or triggers degradation of a disruptor. In some embodiments, activity of the disruptor is reduced by about 10%, 20%, 30%, 40%, 50%, 60%, 70%, 80%, 90%, 91%, 92%, 93%, 94%, 95%, 96%, 97%, 98%, 99%, or more. In some embodiments, the disruptor is amyloid β (Aβ).

The modulator can be any compound that modulates the Syp/Syb complex. In some embodiments, the modulator is selected from the group consisting of small molecules, organic compounds, inorganic compounds, nucleic acids, peptides, peptide mimetics, proteins, antibodies, and antibody fragments. In some embodiments, the modulator is an antibody or antigen-binding fragment thereof The term "antibody" refers to immunoglobulin molecules and immunologically active portions of immunoglobulin molecules, i.e., molecules that contain an antigen binding site that immunospecifically binds an antigen. Also encompassed by the term "antibody" are antibodies comprised of two immunoglobulin heavy chains and two immunoglobulin light chains as well as a variety of forms besides antibodies; including, for example, Fv, Fab, and F(ab)'2, recombinant antibodies, non-human antibodies, chimeric antibodies, humanized antibodies, fully human antibodies, and bifunctional hybrid antibodies. Methods for producing antibodies and fragments thereof are known in the art. See, for example, US Patent Publication 2010/0209432, which is incorporated herein by reference.

In some embodiments, the modulator is a nucleic acid. Non-limiting examples of nucleic acid modulators include expression vectors encoding an active protein or nucleic acid; triggers of RNA interference, such as short-interfering RNA, short-hairpin RNA, and other double-stranded RNA species; and aptamers. Nucleic acid modulators may be naturally occurring sequences isolated from a target organism, recombinantly produced, or chemically synthesized. Recombinant molecular techniques are known to those skilled in the art. See, for example, Maniatis et al. (Molecular Cloning-A Laboratory Manual; Cold Spring Harbor, 1982), D. Glover, ed. (DNA Cloning Vols I, II, and III; IRL Press Ltd.), Sambrook et al. (*Molecular Cloning-A Laboratory Manual*; Cold Spring Harbor Laboratory Press, 1989), and Fred M. Ausubel et al., ed. (*Current Protocols in Molecular Biology (CPMB)*; John Wiley and Sons, Inc.), which are incorporated herein by reference.

In some embodiments, the modulator is a peptide or peptide complex comprising one or more peptides. Peptide modulators may have any length. In some embodiments, a peptide modulator is about, less than about, or more than about 1, 2, 3, 4, 5, 6, 7, 8, 9, 10, 11, 12, 13, 14, 15, 16, 17, 18, 19, 20, 30, 40, 50, 60, 70, 80, 90, 100, 150, 200, 300, 400, 500, 600, 700, 800, 900, 1000, or more amino acids in length. In some embodiments, the peptide comprises a sequence derived from a naturally occurring peptide sequence, such as 1, 2, 3, 4, 5, 6, 7, 8, 9, 10, 11, 12, 13, 14, 15, 16, 17, 18, 19, 20, 30, 40, 50, 60, 70, 80, 90, 100, or more contiguous amino acids, such as the entire sequence of a naturally occurring peptide sequence or splice variants thereof Naturally occurring peptide sequences may be modified to improve function as a modulator of the Syp/Syb complex, such as by disulfide bond formation, glycosylation, lipidation, acetylation, phosphorylation, modification of side chains, and replacement of amino acids with or addition of unnatural or synthetic amino acids, including glycine and both the D or L optical isomers, and amino acid analogs and peptidomimetics. In some embodiments, a peptide modulator comprises a naturally occurring peptide sequence that is modified such that the portion of the peptide modulator comprising the naturally occurring peptide is about, less than about, or more than about 75%, 80%, 85%, 90%, 91%, 92%, 93%, 94%, 95%, 96%, 97%, 98%, 99%, or more identical with the naturally occurring peptide or a fragment thereof. In some embodiments, the naturally occurring sequence is that of ciliary neurotrophic factor (CNTF, SEQ ID NO:21), or a portion thereof.

In some embodiments, the peptide modulator derived from the CTNF can be a peptide comprising 1,2, 3,4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 96, 97, 98, 99 or 100 contiguous amino acids from SEQ ID NO:21. In some embodiments, a peptide modulator derived from SEQ ID NO:21can be a peptide comprising 1-10, 1-15, 1-20, 1-25, 1-30, 1-35, 1-40, 1-45 or 1-50 contiguous amino acids from SEQ ID NO:21. In some embodiments, a peptide modulator derived from contiguous can be a peptide comprising 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 40, 45 or 50 amino acids that are different from the selected sequences from which the peptide is derived. In some embodiments, a peptide modulator derived from contiguous can be a peptide comprising 1, 2, 3,4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 40, 45, or 50 mutations. In some embodiments, a peptide derived modulator from SEQ ID NO:21can be a peptide comprising a mutation at amino acid position 1, 2, 3,4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 96, 97, 98, 99 or 100. In some embodiments, mutations are mutations of non-essential amino acids. In some embodiments, mutations are mutations of essential amino acids. In some embodiments, mutations are mutations of hydrophobic amino acids. In some embodiments, mutations are mutations of naturally occurring amino acids. In some embodiments, mutations are mutations to a conservative amino acid. In some embodiments, a peptide modulator derived from SEQ ID NO: 21 can be a peptide comprising 1,2, 3,4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 40, 45 or 50 amino acid analogues.

In some embodiments, the peptide modulator comprises one or more amino acid sequences selected from SEQ ID NO: 1-20, provided in Table 1:

TABLE 1

Example Peptide Modulator Sequences

| Sequence | ID |
|---|---|
| VGDGGLFEKKL | SEQ ID NO: 1 |
| VGDGGMFEKKM | SEQ ID NO: 2 |
| VGDGGLFEKKL | SEQ ID NO: 3 |
| IGDGGLFEKKL | SEQ ID NO: 4 |
| VGDGGDFQKKM | SEQ ID NO: 5 |
| VGDGGVFETKI | SEQ ID NO: 6 |
| VGDGGVFEQKF | SEQ ID NO: 7 |
| IGQGGMFTKKL | SEQ ID NO: 8 |
| IGDGGRFERRL | SEQ ID NO: 9 |
| VGDGSMFEKKK | SEQ ID NO: 10 |
| VGDGGQFEKEW | SEQ ID NO: 11 |
| IGDGGLFKRKY | SEQ ID NO: 12 |
| IGDGGIIEKEM | SEQ ID NO: 13 |
| VGDGGIIEKEM | SEQ ID NO: 14 |
| VGDGDTFEKKM | SEQ ID NO: 15 |
| IGDGGVFETKI | SEQ ID NO: 16 |
| VGDGGVFETKI | SEQ ID NO: 17 |
| VGDGGLFEAKL | SEQ ID NO: 18 |
| IGDGGVFETKM | SEQ ID NO: 19 |
| IGDGGVFETKI | SEQ ID NO: 20 |

Peptide modulators may be produced by any available means, such as by chemical synthesis, chemical modification, isolation and optional fragmentation of naturally occurring peptides, recombinant production in and isolation from host cells, or combinations of these. Various methods for producing peptides are described in detail herein, and many are known in the art. See, for example, US Published Application 2009/0285810 which is hereby incorporated by reference.

In some embodiments, peptides may be produced by ribosomal synthesis, which utilizes the fundamental methods of transcription and translation to express peptides. Ribosomal synthesis is usually performed by manipulating the genetic code of various expression systems. Some peptides can be expressed in their native form in eukaryotic hosts such as Chinese hamster ovary (CHO) cells. Animal cell culture may require prolonged growing times to achieve maximum cell density and may achieve lower cell density than prokaryotic cell cultures (see Cleland, J. (1993) ACS Symposium Series 526, Protein Folding: In Vivo and In Vitro, American Chemical Society). Bacterial host expression systems such as Escherichia coli may achieve higher productivity than animal cell culture, and may have fewer regulatory hurdles for peptides intended to be used therapeutically. Numerous US patents on general bacterial expression of recombinant proteins exist, including U.S. Pat. No. 4,565,785.

In one embodiment, the expression system is a microbial expression system. For example, in one embodiment, the process uses *E. coli* cells.

In some embodiments, the method of the invention involves the construction of a DNA vector which includes certain selectable markers (such as antibiotic resistance in the case of *E. coli*) enabling selective screening against the cells that do not contain the constructed vector with the gene of interest. Vectors according to the invention may include hybrid promoters and multiple cloning sites for the incorporation of different genes. Various expression vectors may include the pET system and the pBAD system.

The pET system encompasses more than 40 different variations on the standard pET vector. In some embodiments, the pET system utilizes a T7 promoter that is recognized specifically by T7 RNA polymerase. This polymerase can transcribe DNA five times faster than *E. coli* RNA polymerase allowing for increased levels of transcription. In some embodiments, the *Escherichia coli* is protease deficient.

In some embodiments, a vector is designed with a sequence coding for a fusion peptide comprising an inclusion-body directing peptide, an affinity tag peptide, a cleavable peptide, and the peptide modulator of the Syp/Syb complex. For example, in one embodiment, the vector is a pET-19b vector that is modified to include a ketosteroid isomerase (KSI) sequence as the inclusion-body directing peptide. Thus, following cleavage of a restriction site such as the NcoI restriction site and insertion of the KSI sequence, the KSI sequence is flanked by two NcoI restriction sites. In addition, such a vector may be modified to include a histidine tag sequence as the sequence coding for an affinity tag adjacent to a tryptophan-encoding tag sequence as the sequence coding for a cleavable peptide which is further adjacent to a sequence coding for a peptide modulator. If an XhoI restriction site is used for purposes of insertion, the newly inserted sequence is flanked by two XhoI restriction sites. In some embodiments, a vector for the expression of a peptide modulator of a Syp/Syb complex, such as a modified pET-19b vector, contains the desired fusion peptide in a four part sequence: a KSI sequence or functional fragment to sequester the synthesized fusion protein into inclusion bodies, an affinity tag such as hexahistidine, a cleavage tag such as a tryptophan, and the peptide modulator.

Upon construction of an appropriate vector, the vector may be introduced into a host cell according to any method, and expression of a desired peptide may be induced or activated by any method in the art.

In some embodiments, once constructed, a vector according to the invention is inoculated or transformed into competent cells. In various embodiments, the competent cells may be mammalian cells such as Chinese hamster ovary cells, or microbial cells, such as *E. coli* cells. For example, the cells may be commercially available, such as DHS-α *E. coli* cells (available from Invitrogen).

In some embodiments, transformed cells are plated onto agar containing an antibacterial agent to prevent the growth of any cells that do not contain a resistance gene, thereby selecting for cells that have been transformed. In some embodiments, transformed *E. coli* cells are plated onto agar containing ampicillin to prevent the growth of any *E. coli* strains that do not contain the constructed pET-19b vector, and a colony is selected for further expansion.

Colonies from the plating process may be grown in starter culture or broth according to standard cell culture techniques. For example, in some embodiments, one colony from an agar plate is grown in a starter culture of broth, which may optionally contain an antibacterial agent. Typically, cells are grown to a preselected optical density before being further processed to obtain fusion peptide. For example, cells may be grown to an optical density (OD) of about, less than about, or more than about 0.1, 0.2, 0.3, 0.4, 0.5, 0.6, 0.7, 0.8, or 0.9. In some embodiments the cells are grown to an optical density (OD) of about 0.5.

In a bacterial expression system, once the vector-containing bacterial cells have been isolated, inducible transcription may be used to produce the desired fusion peptide. For example, in *E. coli* cells, the lac operon serves as an inducible promoter that is activated under certain environmental conditions. *E. coli* are generally capable of metabolizing the monosaccharide glucose. However, in order to metabolize the disaccharide lactose, the cells need an enzyme known as β-galactosidase. Thus, low extracellular glucose concentrations and high lactose concentrations induce the lac operon and the gene for β-galactosidase is transcribed. Accordingly, in various embodiments, an inducible promoter such as the lac operon is situated upstream from the sequence coding for the fusion peptide. Upon induction of the lac operon, transcription of the sequence coding for the desired peptide occurs.

The term "activation" refers to the removal of repressor protein. A repressor protein is generally allosteric meaning it changes shape when bound by an inducer molecule and dissociates from the promoter. This dissociation allows for the transcription complex to assemble on DNA and initiate transcription of any genes downstream of the promoter. Therefore, by splicing genes produced in vitro into the bacterial genome, one can control the expression of novel genes. This trait may be used advantageously when dealing with inclusion bodies if the production and amassing of inclusion bodies becomes toxic enough to kill *E. coli*. For example, expression of the desired fusion peptide can be delayed until a sufficient population of cells has been cultured, and then the promoter can be induced to express a large amount of fusion peptide by removal of the repressor protein. Thus, the L-arabinose operon may be activated according to the invention for increased protein expression at a desired timepoint. Specifically, the L-arabinose operon may be activated by both the addition of L-arabinose into the growth medium and the addition of IPTG, a molecule that acts as an activator to dissociate the repressor protein from the operator DNA.

In some cases, cells expressing a fusion peptide consisting only of an affinity tag, a cleavable tag, and the target peptide cannot produce large amounts of fusion peptide. The reasons for low production yields may vary. For example, the fusion peptide may be toxic to the bacteria, thus causing the bacteria to die upon production of certain levels of the fusion peptide. Alternatively, the target peptide may be either poorly expressed or rapidly degraded in the bacterial system. In various scenarios, the target peptide may be modified by the host cell, including modifications such as glycosylation. To remedy some or all of these problems, a desired fusion peptide may be directed to an inclusion body, thereby physically segregating the target peptide from degradative factors in the cell's cytoplasm or, in the case of target peptides that are toxic to the host such as peptide antibiotics, physically segregating the target peptide to avoid toxic effects on the host. Moreover, by physically aggregating the fusion peptide in an inclusion body, the subsequent separation of the fusion peptide from the constituents of the host cell and the media (i.e., cell culture or broth) may be performed more easily or efficiently.

Target peptides may be directed to inclusion bodies by producing the target peptide as part of a fusion peptide where the target peptide is linked either directly or indirectly via intermediary peptides with an inclusion-body directing peptide. In various embodiments, an otherwise identical fusion peptide without an inclusion-body directing peptide has minimal or no tendency to be directed to inclusion bodies in an expression system. Alternatively, an otherwise identical fusion peptide without an inclusion-body directing peptide has some tendency to be directed to inclusion bodies in an expression system, but the number, volume, or weight of inclusion bodies is increased by producing a fusion peptide with an inclusion-body directing peptide. In various embodiments, where the target peptide itself directs the fusion peptide of the invention to inclusion bodies, a separate inclusion-body directing peptide may be excluded.

Any inclusion-body directing peptide may be used according to the methods of the invention. For example, methods have been described which allow a-human atrial natriuretic peptide (α-hANP) to be synthesized in stable form in *E. coli*. In one example, eight copies of the synthetic α-hANP gene were linked in tandem, separated by codons specifying a four amino acid linker with lysine residues flanking the authentic N and C-termini of the 28 amino acid hormone. That sequence was then joined to the 3' end of a fragment containing the lac promoter and the leader sequence coding for the first seven N terminal amino acids of β-galactosidase. The expressed multidomain protein accumulated intracellularly into stable inclusion bodies and was purified by urea extraction of the insoluble cell fraction. The purified protein was cleaved into monomers by digestion with endoproteinase lys C and trimmed to expose the authentic C-terminus by digestion with carboxypeptidase B. See Lennick et al., "High-level expression of α-human atrial natriuretic peptide from multiple joined genes in *Escherichia coli*," Gene, 61:103-112 (1987), incorporated by reference herein.

In some embodiments, directing the target peptide to an inclusion body by producing the target peptide as part of a fusion peptide may lead to higher output of peptide. For example, in various embodiments, a desired peptide is produced in concentrations greater than about 100 mg/L. In some embodiments, a desired peptide is produced in concentrations greater than about 200 mg/L, 250 mg/L, 300 mg/L, 350 mg/L, 400 mg/L, 450 mg/L, 500 mg/L, 550 mg/L, 600 mg/L, 650 mg/L, 700 mg/L, 750 mg/L, 800 mg/L, 850 mg/L, 900 mg/L, 950 mg/L, 1 g/L, 1.5 g/L, 2 g/L, 2.5 g/L, or more. In some embodiments, the output of a desired peptide is in a range from about 500 mg/L to about 2 g/L, or from about 1 g/L to about 2.5 g/L. In one embodiment, the desired fusion peptide is produced in yields equal to or greater than 500 mg/L of media.

In one embodiment, the inclusion-body directing peptide is a ketosteroid isomerase (KSI) or inclusion-body directing functional fragment thereof In certain embodiments, inclusion-body directing functional fragment comprises about, less than about, or more than about 25, 30, 35, 40, 45, 50, 55, 60, 65, 70, 75, 80, 85, 90, 95, 100, or more amino acids. Homologs of a ketosteroid isomerase are also encompassed.

Such homologs may have at least 25%, 30%, 35%, 40%, 45%, 50%, 55%, 60%, 65%, 70%, 75%, 80%, 85%, 90%, 95%, or more sequence identity with the amino acid sequence of a ketosteroid isomerase or functional portion thereof In various embodiments, an expression system for a fusion peptide with a functional fragment or homolog of a ketosteroid isomerase will produce at least 25%, 30%, 35%, 40%, 45%, 50%, 55%, 60%, 65%, 70%, 75%, 80%, 85%, 90%, 95%, 100%, or more of the amount of inclusion bodies produced by an otherwise identical expression system with a fusion peptide containing a complete ketosteroid isomerase peptide sequence.

In one embodiment, a desired peptide is made through solid phase peptide synthesis (SPPS). SPPS involves covalently linking a short peptide to an insoluble polymer providing a structural support for the elongation of the peptide. To achieve elongation of the peptide, the practitioner performs a series of repeated cycles de-protecting the chemically reactive portions of amino acids, linking the de-protected free terminal amine (N) to a single N-protected amino acid, de-protecting the N-terminal amine of the newly added residue, and repeating this process until the desired peptide has been built. Additional measures may be necessary for peptides that are about 50 or more amino acids in length.

In one embodiment, solid phase peptide synthesis uses Fmoc protecting groups. The Fmoc protecting group utilizes a base labile alpha-amino protecting group. In an alternative embodiment, the solid phase peptide synthesis uses Boc protecting groups. The Boc protecting group is an acid labile alpha-amino protecting group. Each method may involve distinct resin addition, amino acid side-chain protection, and consequent cleavage/deprotection steps. Generally, Fmoc chemistry generates peptides of higher quality and in greater yield than Boc chemistry. Impurities in Boc-synthesized peptides are mostly attributed to cleavage problems, dehydration and t-butylation. Once assembled on the solid support, the peptide is cleaved from the resin using strongly acidic conditions, usually with the application of trifluoracetic acid (TFA). It is then purified using reverse phase high pressure liquid chromatography, or RP-HPLC, a process in which sample is extruded through a densely packed column and the amount of time it takes for different samples to pass through the column (known as a retention time) is recorded. As such, impurities are separated out from the sample based on the principle that smaller peptides pass through the column with shorter retention times and vice versa. Thus, the protein being purified elutes with a characteristic retention time that differs from the rest of the impurities in the sample, thus providing separation of the desired protein.

Solid-phase peptide synthesis generally provides high yields because excess reagents can be used to force reactions to completion. Separation of soluble byproducts is simplified by the attachment of the peptide to the insoluble support throughout the synthesis. Because the synthesis occurs in the same vessel for the entire process, mechanical loss of material is low.

In some embodiments, an inclusion body directing peptide may be excluded. Alternatively, an inclusion body directing peptide may be included to provide beneficial folding properties and/or solubility/aggregating properties.

In some embodiments, liquid phase methods or solution phase methods of synthesis are used to carry out all reactions in a homogeneous phase. Successive amino acids may be coupled in solution until the desired peptide material is formed. In various embodiments, successive intermediate peptides are purified by precipitation and/or washes. Peptides and amino acids from which peptides are synthesized may have reactive side groups as well as reactive terminal ends. Undesired reactions at side groups or at the wrong terminal end of a reactant may undesirable by-products, sometimes in significant quantities. To minimize side reactions, various embodiments may mask reactive side groups and terminal ends of reactants to help ensure that the desired reaction occurs. In various embodiments, the employed methods for peptide bond formation in solution may include: the carbodiimide method (DCC, DIC), symmetric or mixed anhydrides, active esters (OPfp, Odhbt, OSu), phosphonium salts (BOP, PyBOP, AOP, PyAOP) and uronium/guanidinium-mediated salt and processes using HOBt and HAOt (HBTU, HATU, HBPyU, etc).

In some embodiments, peptides may be produced by non-ribosomal synthesis. Such peptides include circular peptides and/or depsipeptides.

Nonribosomal peptides can be synthesized by one or more nonribosomal peptide synthetase (NRPS) enzymes. These enzymes are independent of messenger RNA. Nonribosomal peptides often have a cyclic and/or branched structure, can contain non-proteinogenic amino acids including D-amino acids, carry modifications like N-methyl and N-formyl groups, or are glycosylated, acylated, halogenated, or hydroxylated. Cyclization of amino acids against the peptide backbone is often performed, resulting in oxazolines and thiazolines; these can be further oxidized or reduced. On occasion, dehydration is performed on serines, resulting in dehydroalanine.

Following production of a desired peptide, separation from the production media may be required. Optionally, following separation, the desired peptide and carrier may be concentrated to remove excess liquid. Numerous methods for separating fusion peptides from their formation media and subsequent handling may be adapted to the invention. Examples of purification methods include one or more of cell lysis, pelleting of encapsulating inclusion bodies, solubilization of encapsulating inclusion bodies, affinity chromatography, and cleavage of a cleavage tag included in the fusion protein.

In one aspect, the invention provides a composition comprising a compound of the invention in an amount sufficient to treat Alzheimer's disease (AD), such as an amount of an agent that is sufficient to effect beneficial or desired results. A therapeutically effective amount will vary depending upon the subject and disease stage being treated, the weight and age of the subject, gender of the subject, the severity of the disease condition, the manner of administration and the like, which can readily be determined by one of ordinary skill in the art. The specific dose will vary depending on the particular agent chosen, the dosing regimen to be followed, whether it is administered in combination with other compounds, timing of administration, and the physical delivery system in which it is carried. In general, treatment of AD may comprise slowing, stopping, or reversing disease progression, such as may be measured with respect to a sign or symptom of AD, and/or increasing survival time. In some embodiments, AD may be treated prophylactically so as to delay or prevent the onset of AD in a subject at risk for developing the disease. Examples of signs or symptoms of AD that may be assessed include, but are not limited to, enhancement of microglial activity; infiltration and/or accumulation of microglia in the brain, in particular, in senile plaques; accumulation of substances activated upon inflammation, e.g., complements, in the brain; accumulation and/or deposition of Aβ in brain tissues; impairment of learning;

mild to severe dementia; progressive impairment of memory (ranging from mild forgetfulness to disorientation and severe memory loss); poor visio-spatial skills; personality changes; poor impulse control; poor judgment; distrust of others; increased stubbornness; restlessness; poor planning ability; poor decision making; and social withdrawal; extracellular neuritic β-amyloid plaques; neurofibrillary tangles; neurofibrillary degeneration; granulovascular neuronal degeneration; synaptic loss; and neuronal cell death.

In some embodiments, a composition for treating AD further comprises a pharmaceutically acceptable excipient, carrier, or stabilizer. Examples of pharmaceutically acceptable excipients, carriers, and stabilizers are known in the art, the choice of which may depend on the choice of compound with which it is combined, the specific formulation, and/or the mode of delivery. See e.g. *Remington's Pharmaceutical Sciences* 16th edition, Osol, A. Ed. (1980). In general, an acceptable excipient, carrier, or stabilizer is non-toxic to the recipient at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low-molecular-weight (e.g. less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

Methods of Treating Alzheimer'S Disease

In one aspect, the invention provides a method for treating Alzheimer's disease (AD). In one embodiment, the method comprises administering to a subject in need thereof a pharmaceutical composition comprising a compound of the invention. In one embodiment, the method comprises administering to a subject in need thereof a pharmaceutical composition comprising a modulator that modulates a complex comprising synaptophysin and/or synaptobrevin (Syp/Syb complex) in an amount sufficient to treat AD. In one embodiment, the method comprises administering to a subject in need thereof a pharmaceutical composition comprising a modulator that inhibits the disruption of a complex by amyloid β (Aβ) in an amount sufficient to treat AD, wherein the complex comprises Syp and Syb.

In general, treatment of AD may comprise slowing, stopping, or reversing disease progression, such as may be measured with respect to a sign or symptom of AD, and/or increasing survival time. In some embodiments, AD may be treated prophylactically so as to delay or prevent the onset of AD in a subject at risk for developing the disease. Examples of signs or symptoms of AD that may be assessed include, but are not limited to, enhancement of microglial activity; infiltration and/or accumulation of microglia in the brain, in particular, in senile plaques; accumulation of substances activated upon inflammation, e.g., complements, in the brain; accumulation and/or deposition of Aβ in brain tissues; impairment of learning; mild to severe dementia; progressive impairment of memory (ranging from mild forgetfulness to disorientation and severe memory loss); poor visio-spatial skills; personality changes; poor impulse control; poor judgment; distrust of others; increased stubbornness; restlessness; poor planning ability; poor decision making; and social withdrawal; extracellular neuritic β-amyloid plaques; neurofibrillary tangles; neurofibrillary degeneration; granulovascular neuronal degeneration; synaptic loss; and neuronal cell death. For example, a therapeutically effective amount preferably refers to an amount of a therapeutic agent that decreases the symptoms of AD, increases the time to progression of the symptoms of AD, or increases survival time by at least about 5%, 10%, 15%, 20%, 25%, 30%, 35%, 40%, 45%, 50%, 55%, 60%, 65%, 70%, 75%, 80%, 85%, 90%, 95%, or 100%, or more as compared to that which would have occurred without the present invention, or with respect to a corresponding measure or trajectory prior to such treatment. Changes in a pathology associated with AD can be measured in tissue samples from subjects by comparing one or more samples acquired before treatment to one or more samples after treatment. In some embodiments, administration of the pharmaceutical composition stabilizes a pathological characteristic of AD, or decreases a pathological characteristic by 5%, 10%, 15%, 20%, 25%, 30%, 35%, 40%, 45%, 50%, 55%, 60%, 65%, 70%, 75%, 80%, 85%, 90%, 95%, or more. In some embodiments, the pathological characteristic of AD is the level of Aβ.

The therapeutic methods of the invention may be carried out on subjects displaying pathology resulting from AD, subjects suspected of displaying pathology resulting from AD, and subjects at risk of displaying pathology resulting from AD. For example, subjects that have a genetic predisposition to AD can be treated prophylactically. Subjects exhibiting AD symptoms may be treated to decrease the symptoms or to slow down or prevent further progression of the symptoms. In general, the physical changes associated with increasing severity of AD are progressive. Thus, in one embodiment of the invention, subjects exhibiting mild signs of AD pathology (e.g., corresponding to mild cognitive impairment or Braak stages 1-3) may be treated to improve the symptoms and/or prevent further progression of the symptoms.

Cognitive behavior in AD (e.g., mentation, memory) may be measured by any one of several tests (See Gershon et al., *Clinical Evaluation of Psychotropic Drugs: Principles and Guidelines*, Prien and Robinson (eds.), Raven Press, Ltd., New York, 1994, p. 467). One such test, BCRS, is designed to measure only cognitive functions: concentration, recent memory, past memory, orientation, functioning, and self-care. This test, as well as the Weschler Memory Scale and the Alzheimer's Disease-Associated Scale, may be used to determine improvement following therapeutic treatment. An increase in mentation or a reduction in memory loss is present if there is a statistically significant difference in the direction of normality in the Weschler Memory Scale test. For example, test results of the performance of treated patients are compared to members of a placebo group or between subsequent tests given to the same patient.

A frequently used instrument to evaluate cognitive impairment is the Mini-Mental State Examination (MMSE) (see Cockrell, J. R., et al., Psychopharmacology 1988; 24:689-692, Crumb, R. M., et al., JAMA 1993; 269:2386-2391). The MMSE includes measures of memory, orientation to place and time, naming, reading, copying (visuospatial organization), writing, and the ability to follow a three-stage command. A score of less than 24 points on the MMSE is generally accepted as signifying cognitive impairment.

Other measures of AD severity include the Blessed Orientation Memory Concentration instrument, the Short Test of Mental Status, and the Functional Activities Questionnaire. The Blessed Information Memory Concentration instrument (Blessed, G., et al., Br. J. Psychiatry 1968; 114:797-811) primarily evaluates orientation, memory, and concentration. The Blessed Orientation Memory Concentration instrument (Katzman, R., et al., Am. J. Psychiatry 1983; 140:734-739) assesses orientation to time, recall of a short phrase, the ability to count backward, and the ability to recite months in reverse order. The Short Test of Mental Status (Kokmen, E., et al., Mayo Clin. Proc., 1987; 62(4):281-289) evaluates orientation, attention, recall, concentration, abstraction, clock drawing, and copying. The Functional Activities Questionnaire (Pfeffer, R. I., et al., J. Gerontol. 1982; 37:323-329) employs responses from a family member or a friend of the subject to evaluate functional activities that may be impaired by dementia. In some embodiments, treatment of AD stabilizes a measure of disease severity for at least about 1, 2, 3, 4, 5, 6, 7, 8, 9, 10, 11, 12, or more months; or at least about 1, 2, 3, 4, 5, 6, 7, 8, 9, 10, 15, 20, or more years, such that steady worsening by the measure is slowed or prevented. In some embodiments, treatment of AD improves a measure of disease severity by 5%, 10%, 15%, 20%, 25%, 30%, 35%, 40%, 45%, 50%, 60%, 70%, 80%, 90%, 95%, 99%, 100%, or more.

The compounds and pharmaceutical compositions thereof may be administered by any means that achieve their intended purpose. For example, administration may be by oral, parenteral, subcutaneous, intravenous, intramuscular, intraperitoneal, transdermal, buccal, intrathecal, intracranial, intranasal, or topical routes. The dosage administered may be dependent upon the age, health, and weight of the recipient, kind of concurrent treatment, if any, frequency of treatment, and the nature of the effect desired. Compounds and compositions of the invention may be administered according to a regular schedule, may be administered on an as-needed basis as determined by a medical practitioner, or a combination of these. Compounds and compositions of the invention may be administered once or more than once every 1, 2, 3, 4, 5, 6, 7, 8, 9, 10, 11, 12, 13, 14, or more days; once or more than once every 1, 2, 3, 4, 5, 6, 7, 8, or more weeks; once or more than once every 1, 2, 3, 4, 5, 6, 7, 8, 9, 10, 11, 12, or more months; once or more than once every 1, 2, 3, 4, 5, or more years; or a combination of these, such as more frequently during a first period than during a second period. Administration of a compound or composition of the invention may be combined with administration of a second compound or composition. Such combination may be in the form of a single composition for co-administration. Alternatively, the second compound or composition may be administered separately, either at substantially the same time as a compound or composition of the invention, or spaced at a defined interval. In some embodiments, the pharmaceutical composition further comprises an enhancer compound that enhances the ability of a modulator of a Syp/Syb complex to cross the blood-brain barrier. In some embodiments, the enhancer and the modulator are part of a single fusion peptide. In some embodiments, the enhancer is covalently attached to the modulator. Examples of compounds that may be included in pharmaceutical compositions of the invention are disclosed in WO 2002/004451, which claims priority to U.S. 60/216,808

Methods of Inhibiting Synaptophysin Degradation

In various embodiments, a method is provided for inhibiting synaptophysin degradation in vivo comprising administering to a patient in need thereof an exogenous substrate of SIAH-1/2 wherein SIAH-1/2 acts on the exogenous substrate. Without wishing to be bound by theory, it is believed that the exogenous substrate competes with synaptophysin as a substrate for the E3 or SIAH-1/2 pathway of ubiquitylation and subsequent degradation. By competing with synaptophysin, the exogenous substrate interferes with the signaling pathway marking synaptophysin for degradation, thus blocking or reducing the degradation of synaptophysin. In various embodiments, the synaptophysin degradation may be inhibited by an amount selected from greater than 10%, 20%, 30%, 40%, 50%, 60%, 70%, 80%, or 90%. In various embodiments, the exogenous substrate is a peptide or a small-molecule mimic of a peptide. The patient in need thereof may have or may be at risk of having Alzheimer's Disease. By administering the exogenous substrate, the symptoms and/or pathology associated with Alzheimer's Disease may be treated, or the progression of the disease may be altered.

Pharmaceutical Compositions

The compounds of the disclosure are typically formulated to provide a therapeutically effective amount of compound as the active ingredient, or a pharmaceutically acceptable salt, ester, prodrug, solvate, hydrate or derivative thereof Where desired, the pharmaceutical compositions contain pharmaceutically acceptable salt and/or coordination complex thereof, and one or more pharmaceutically acceptable excipients, carriers, including inert solid diluents and fillers, diluents, including sterile aqueous solution and various organic solvents, permeation enhancers, solubilizers and adjuvants.

In some embodiments, the concentration of one or more of the compounds disclosed herein in the pharmaceutical compositions of the present invention is less than 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v or v/v.

In some embodiments, the concentration of one or more of the compounds disclosed herein in the pharmaceutical compositions of the present invention is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v, or v/v.

In some embodiments, the concentration of one or more one or more of the compounds disclosed herein in the pharmaceutical compositions of the present invention is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v. v/v.

In some embodiments, the amount of one or more compounds disclosed herein in 1 mL of the pharmaceutical compositions of the present invention is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of one or more compounds disclosed herein in 1 mL of the pharmaceutical compositions of the present invention is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5g, 7 g, 7.5g, 8 g, 8.5 g, 9 g, 9.5 g, or 10 g.

In some embodiments, the amount of one or more compound of the present invention in 1 mL of the pharmaceutical compositions is in the range of 0.0001-10 g, 0.0005-9 g, 0.001-8 g, 0.005-7 g, 0.01-6 g, 0.05-5 g, 0.1-4 g, 0.5-4 g, or 1-3 g.

The compounds according to the invention are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. An exemplary dosage is 100 to 2000 mg per day. The exact dosage will depend upon the route of administration, the form in which the compound is administered, the subject to be treated, the body weight of the subject to be treated, and the preference and experience of the attending physician.

Described below are non-limiting exemplary pharmaceutical compositions and methods for preparing the same. Pharmaceutical compositions for oral administration: In some embodiments, the invention provides a pharmaceutical composition for oral administration containing a compound of the present invention, and a pharmaceutical excipient suitable for oral administration.

In some embodiments, the invention provides a solid pharmaceutical composition for oral administration containing: (i) an effective amount of a compound of the present invention; optionally (ii) an effective amount of a second agent; and (iii) one or more pharmaceutical excipients suitable for oral administration. In some embodiments, the composition further contains: (iv) an effective amount of a third agent.

In some embodiments, the pharmaceutical composition may be a liquid pharmaceutical composition suitable for oral consumption. Pharmaceutical compositions of the invention suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion. Such dosage forms can be prepared by any of the methods of pharmacy, but all methods include the step of bringing the active ingredient into association with the carrier, which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

This invention further encompasses anhydrous pharmaceutical compositions and dosage forms comprising an active ingredient. Anhydrous pharmaceutical compositions and dosage forms of the invention can be prepared using anhydrous or low moisture containing ingredients and low moisture or low humidity conditions. Pharmaceutical compositions and dosage forms of the invention which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

An active ingredient can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the compositions of the invention to provide tablets that disintegrate when exposed to an aqueous environment. Too much of a disintegrant may produce tablets which may disintegrate in the bottle. Too little may be insufficient for disintegration to occur and may thus alter the rate and extent of release of the active ingredient(s) from the dosage form. Thus, a sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethylaureate, agar, or mixtures thereof. Additional lubricants include, for example, a syloid silica gel, a coagulated aerosol of synthetic silica, or mixtures thereof A lubricant can optionally be added, in an amount of less than about 1 weight percent of the pharmaceutical composition.

In some cases, colloid particles include at least one cationic agent and at least one non-ionic surfactant such as a poloxamer, tyloxapol, a polysorbate, a polyoxyethylene castor oil derivative, a sorbitan ester, or a polyoxyl stearate. In some cases, the cationic agent is an alkylamine, a tertiary alkyl amine, a quaternary ammonium compound, a cationic lipid, an amino alcohol, a biguanidine salt, a cationic compound or a mixture thereof In some cases the cationic agent is a biguanidine salt such as chlorhexidine, polyaminopropyl biguanidine, phenformin, alkylbiguanidine, or a mixture thereof In some cases, the quaternary ammonium compound is a benzalkonium halide, lauralkonium halide, cetrimide, hexadecyltrimethylammonium halide, tetradecyltrimethylammonium halide, dodecyltrimethylammonium halide, cetrimonium halide, benzethonium halide, behenalkonium halide, cetalkonium halide, cetethyldimonium halide, cetylpyridinium halide, benzododecinium halide, chlorallyl methenamine halide, myristylalkonium halide, stearalkonium halide or a mixture of two or more thereof In some cases, cationic agent is a benzalkonium chloride, lauralkonium chloride, benzododecinium bromide, benzethenium chloride, hexadecyltrimethylammonium bromide, tetradecyltrimethylammonium bromide, dodecyltrimethylammonium bromide or a mixture of two or more thereof In some cases, the oil phase is mineral oil and light mineral oil, medium chain triglycerides (MCT), coconut oil; hydrogenated oils comprising hydrogenated cottonseed oil, hydrogenated palm oil, hydrogenate castor oil or hydrogenated soybean oil; polyoxyethylene hydrogenated castor oil derivatives comprising poluoxyl-40 hydrogenated castor oil, polyoxyl-60 hydrogenated castor oil or polyoxyl-100 hydrogenated castor oil.

When aqueous suspensions and/or elixirs are desired for oral administration, the active ingredient therein may be combined with various sweetening or flavoring agents, coloring matter or dyes and, if so desired, emulsifying and/or suspending agents, together with such diluents as water, ethanol, propylene glycol, glycerin and various combinations thereof The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactant which can be used to form pharmaceutical compositions and dosage forms of the invention include, but are not limited to, hydrophilic surfactants, lipophilic surfactants, and mixtures thereof That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant may generally have an HLB value of at least 10, while suitable lipophilic surfactants may generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but are not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In one embodiment, the composition may include a solubilizer to ensure good solubilization and/or dissolution of the compound of the present invention and to minimize precipitation of the compound of the present invention. This can be especially important for compositions for non-oral use, e.g., compositions for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropyl alcohol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, e-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, e-caprolactone and isomers thereof, δ-valerolactone and isomers thereof, β-butyrolactone and isomers thereof; and other solubilizers known in the art, such as dimethyl acetamide, dimethyl isosorbide, N-methyl pyrrolidones, monooctanoin, diethylene glycol monoethyl ether, and water. In various embodiments, a solubilizer comprising polyglycol mono- and di-esters of 12-hydroxystearic acid and about 30% free polyethylene glycol (available as Solutol HS 15) is used as a solubilizer.

Mixtures of solubilizers may also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a subject using conventional techniques, such as distillation or evaporation. Thus, if present, the solubilizer can be in a weight ratio of 10%, 25%, 50%, 100%, or up to about 200% by weight, based on the combined weight of the drug, and other excipients. If desired, very small amounts of solubilizer may also be used, such as 5%, 2%, 1% or even less. Typically, the solubilizer may be present in an amount of about 1% to about 100%, more typically about 5% to about 25% by weight.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl) aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Example may include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

Pharmaceutical compositions for injection. In some embodiments, the invention provides a pharmaceutical composition for injection containing a compound of the present invention and a pharmaceutical excipient suitable for injection. Components and amounts of agents in the compositions are as described herein.

The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound of the present invention in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

Pharmaceutical compositions for topical (e.g., transdermal) delivery. In some embodiments, the invention provides a pharmaceutical composition for transdermal delivery containing a compound of the present invention and at least one pharmaceutical excipient suitable for transdermal delivery.

Compositions of the present invention can be formulated into preparations in solid, semi-solid, or liquid forms suitable for local or topical administration, such as gels, water soluble jellies, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation may provide more immediate exposure of the active ingredient to the chosen area.

The pharmaceutical compositions also may comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation. Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Another exemplary formulation for use in the methods of the present invention employs transdermal delivery devices ("patches"). Such transdermal patches may be used to provide continuous or discontinuous infusion of a compound of the present invention in controlled amounts, either with or without another agent.

The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

Pharmaceutical compositions for inhalation. Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

Other pharmaceutical compositions. Pharmaceutical compositions may also be prepared from compositions described herein and one or more pharmaceutically acceptable excipients suitable for sublingual, buccal, rectal, intraosseous, intraocular, intranasal, epidural, or intraspinal administration. Preparations for such pharmaceutical compositions are well-known in the art. See, e.g., See, e.g., Anderson, Philip 0.; Knoben, James E.; Troutman, William G, eds., Handbook of Clinical Drug Data, Tenth Edition, McGraw-Hill, 2002; Pratt and Taylor, eds., *Principles of Drug Action*, Third Edition, Churchill Livingston, N.Y., 1990; Katzung, ed., *Basic and Clinical Pharmacology*, Ninth Edition, McGraw Hill, 20037ybg; Goodman and Gilman, eds., *The Pharmacological Basis of Therapeutics*, Tenth Edition, McGraw Hill, 2001; *Remingtons Pharmaceutical Sciences*, 20th Ed., Lippincott Williams & Wilkins., 2000; Martindale, *The Extra Pharmacopoeia*, Thirty-Second Edition (The Pharmaceutical Press, London, 1999); all of which are incorporated by reference herein in their entirety.

Assays

In one aspect, the invention provides an assay for the identification of compounds for treating Alzheimer's disease. In one embodiment, the assay comprises contacting a cell with a test compound, determining a level of a complex comprising synaptophysin and/or synaptobrevin (Syp/Syb complex), and identifying the test compound as a compound for the treatment of Alzheimer's disease based on the level. In one embodiment, the assay comprises contacting a cell with a test compound, determining a level of a complex comprising synaptophysin and synatobrevin, and identifying the test compound as a compound for the treatment of Alzheimer's disease based on a level of inhibition of disruption of the complex by amyloid $\beta$. In some embodiments, the test compound is selected from the group consisting of small molecules, organic compounds, inorganic compounds, nucleic acids, peptides, peptide mimetics, proteins, antibodies, and antibody fragments. In some embodiments, the test compound is selected from a known library of compounds. In some embodiments, multiple test compounds are assayed simultaneously.

In some embodiments, the assay is an in vivo assay, and the cell that is contacted with a test compound is part of a living organism, such as a mouse, a rat, a rabbit, a dog, a non-human primate, or a human. In some embodiments, the organism is a transgenic mouse model of AD. Examples of mouse models of AD include, but are not limited to, 5XFAD (B6SJL-Tg(APPSwFlLon, PSEN1*M146L*L286V) 6799Vas/J) and 3XTG (B6;129-Psen1tm1Mpm Tg(APPSwe,tauP301L)1Lfa/J). Contacting the cell with a test compound may comprise administering the test compound by oral, parenteral, subcutaneous, intravenous, intramuscular, intraperitoneal, transdermal, buccal, intrathecal, intracranial, intranasal, or topical routes. Determining the level of a Syp/Syb complex may subsequently be accomplished by removing a tissue comprising the cell, such as a brain biopsy, from the organism and measuring the level of the complex according to a method discussed herein.

In some embodiments, the assay is an in vitro assay, and the cell that is contacted with a test compound is in an assay container, such as in a cell culture. Cells may be primary cells or cell lines, and may optionally be genetically modified, such as expressing one or more recombinant transgenes. A cell for use in an assay of the invention can be any that comprises a Syp/Syb complex, or any cell that can be manipulated so as to comprise a Syp/Syb complex, such as by genetic manipulation to express Syp, Syb, and optionally one or more additional members of a Syp/Syb complex. Recombinant techniques and many cell lines are known in the art. Non-limiting examples of cell lines useful in the assay of the invention include C8161, CCRF-CEM, MOLT, mIMCD-3, NHDF, HeLa-S3, Huh1, Huh4, Huh7, HUVEC, HASMC, HEKn, HEKa, MiaPaCell, Panc 1, PC-3, TF1, CTLL-2, C1R, Rat6, CV1, RPTE, A10, T24, J82, A375, ARH-77, Calu1, SW480, SW620, SKOV3, SK-UT, CaCo2, P388D1, SEM-K2, WEHI-231, HB56, TIB55, Jurkat, J45.01, LRMB, Bc1-1, BC-3, IC21, DLD2, Raw264.7, NRK, NRK-52E, MRCS, MEF, Hep G2, HeLa B, HeLa T4, COS, COS-1, COS-6, COS-M6A, BS-C-1 monkey kidney epithelial, BALB/3T3 mouse embryo fibroblast, 3T3 Swiss, 3T3-L1, 132-d5 human fetal fibroblasts; 10.1 mouse fibroblasts, 293-T, 3T3, 721, 9L, A2780, A2780ADR, A2780cis, A172, A20, A253, A431, A-549, ALC, B16, B35, BCP-1 cells, BEAS-2B, bEnd.3, BHK-21, BR 293, BxPC3, C3H-10T1/2, C6/36, Cal-27, CHO, CHO-7, CHO-IR, CHO-K1, CHO-K2, CHO-T, CHO Dhfr -/-, COR-L23, COR-L23/CPR, COR-L23/5010, COR-L23/R23, COS-7, COV-434, CML T1, CMT, CT26, D17, DH82, DU145, DuCaP, EL4, EM2, EM3, EMT6/AR1, EMT6/AR10.0, FM3, H1299, H69, HB54, HB55, HCA2, HEK-293, HeLa, Hepa1c1 c7, HL-60, HMEC, HT-29, Jurkat, JY cells, K562 cells, Ku812, KCL22, KG1, KYO1, LNCap, Ma-Mel 1-48, MC-38, MCF-7, MCF-10A, MDA-MB-231, MDA-MB-468, MDA-MB-435, MDCK II, MDCK II, MOR/0.2R, MONO-MAC 6, MTD-1A, MyEnd, NCI-H69/CPR, NCI-H69/LX10, NCI-H69/LX20, NCI-H69/LX4, NIH-3T3, NALM-1, NW-145, OPCN/OPCT cell lines, Peer, PNT-1A/PNT 2, RenCa, RIN-5F, RMA/RMAS, Saos-2 cells, Sf-9, SkBr3, T2, T-47D, T84, THP1 cell line, U373, U87, U937, VCaP, Vero cells, WM39, WT-49, X63, YAC-1, YAR, PC12, and transgenic varieties thereof Cell lines are available from a variety of sources known to those with skill in the art (see, e.g., the American Type Culture Collection (ATCC) (Manassus, Va.)).

In some embodiments, a cell is contacted with one or more disruptors of the S /Syb complex before, during, or after contacting the cell with a test compound. In some embodiments, the disruptor is Aβ, or a fragment thereof, such as at least about 10, 20, 30, 40, 41, 42, or 43 amino acids of Aβ. In some embodiments, the cell is treated with one or more disruptors comprising amino acids 1-40 of Aβ, a disruptor comprising 1-42 of Aβ, or a combination of these. In some embodiments, the cell naturally expresses Aβ. In some embodiments, the cell expresses a transgenic Aβ. In some embodiments, the Aβ is a recombinant protein, such as a labeled protein. In some embodiments, the label is a fluorescent label. In some embodiments, the assay further comprises determining a level of Aft In some embodiments, a test compound is identified as a compound for the treatment of AD based on a decrease in the level of Aβ of about or at least about 0%, 5%, 10%, 15%, 20%, 25%, 30%, 40%, 50%, 60%, 70%, 80%, 90%, 95%, or more, compared to a reference amount, a starting amount, or a control. In some embodiments, a test compound is identified as a compound for the treatment of AD based on an increase of Aβ of less than about 0%, 5%, 10%, 15%, 20%, 25%, 30%, 40%, 50%, 60%, 70%, 80%, 90%, or 95%, compared to a reference amount, a starting amount, or a control.

Determining the level of a Syp/Syb complex can comprise any suitable protein detection means known in the art. In some embodiments, a Syp/Syb complex is detected intact. In some embodiments, one or more components of the complex are detected individually. In some embodiments, the level of the Syp/Syb complex is determined using a measure of the level of Syp, Syb, or both. In some embodiments, a ratio of Syp to Syb is used as a measure of the level of a Syp/Syb complex.

In some embodiments, the level of Syp/Syb complex is determined for a cell extract. Methods for extracting proteins and detecting proteins in extracts are known in the art. Examples of protein detection methods for use in combination with protein extracts include, but are not limited to, immunosorbent assays, immunoprecipitation assays, Western blot, ELISA, protein arrays, other binding partner assays, and mass spectrometry analyses. In some embodiments, one or more members of a Syp/Syb complex are detected in an extract using one or more probes capable of binding to the one or members of the complex. In some embodiments, the probe is an antibody. In some embodiments the antibody is an unlabeled primary antibody, which itself is detected by binding a secondary antibody that is labeled. In some embodiments, a labeled antibody binds the one or members of the Syp/Syb complex directly. Various suitable labels are known in the art, and include without limitation radioactive labels, fluorescent labels, and dye-converting enzyme labels. In some embodiments, one or members of a Syp/Syb complex are expressed in the cell as a labeled recombinant protein that can be detected directly in an extract. In some embodiments, synaptophysin, synaptobrevin, or both are labeled. In some embodiments, the label is a fluorescent label. In some embodiments, both Syp and Syb are fluorescently labeled, such that changes in the level of interaction between Syp and Syb are detected as changes in fluorescence resonance energy transfer (FRET), such as an increase or decrease of FRET fluorescence relative to a control.

In some embodiments, the level of Syp/Syb complex is determined within a cell, without extracting the complex from the cell. The cell may be alive or dead, fixed or unfixed, and/or permeabilized or non-permeabilized. Methods for detecting proteins in cells are known in the art, including, but not limited to, immunohisochemistry, flow cytometry, fluorescence activated cell sorting (FACS), and other binding partner assays utilizing cells. In some embodiments, one or members of a Syp/Syb complex are expressed in the cell as a labeled recombinant protein that can be detected directly in the cell. In some embodiments, synaptophysin, synaptobrevin, or both are labeled. In some embodiments, the label is a fluorescent label. In some embodiments, both Syp and Syb are fluorescently labeled, such that changes in the level of interaction between Syp and Syb are detected as changes in fluorescence resonance energy transfer (FRET), such as an increase or decrease of FRET fluorescence relative to a control.

In some embodiments, a test compound is identified as a compound for the treatment of AD based on an increase in the level of Syp/Syb complex, or in the level one or more members thereof, of about or at least about 0%, 5%, 10%, 15%, 20%, 25%, 30%, 40%, 50%, 60%, 70%, 80%, 90%, 95%, or more, compared to a reference amount, a starting amount, or a control. In some embodiments, a test compound is identified as a compound for the treatment of AD based on an increase in the level of Syp/Syb complex, or in the level one or more members thereof, of about or at least about 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 1000-fold, 10000-fold, or more, compared to a reference amount, a starting amount, or a control. In some embodiments, a test compound is identified as a compound for the treatment of AD based on a decrease in the level of Syp/Syb complex that is about or less than about 0%, 5%, 10%, 15%, 20%, 25%, 30%, 40%, 50%, 60%, 70%, 80%, 90%, or 95% compared to a reference amount, a starting amount, or a control. A starting amount to which the level of Syp/Syb complex is compared can the level of Syp/Syb complex in the same cell prior to contacting the cells with the test compound, or a reference cell under similar conditions as the test cell that is not contacted with the test compound. In some embodiments, the level of Syp/Syb complex in a cell contacted with a test compound is compared to a level of Syp/Syb complex in a control cell. In general, a control cell is one that receives a treatment similar to a test cell, except that it is not exposed to the test compound. In some embodiments, the control cell is an untreated cell. In some embodiments, both a test cell (i.e. a cell that is contacted with a test compound) and a control cell are contacted with a disruptor of Syp/Syb complex, and only the test cell is contacted with a test compound. I single control cell or set of control cells may be used as a basis for comparison to multiple test cells, each test cell being contacted with a different test compound.

In some embodiments, each of a plurality of cells is contacted separately with a plurality of different test compounds. In general, the contacting step takes place in a separate container for each of the test compounds. Containers can be any suitable container for carrying out the reaction, such as tubes, flow cells, wells of a micro-well plate, or chambers in a microfluidic device. Reactions in wells can be in any suitable format, including plates having 6, 12, 24, 48, 96, 192, 384, 768, 1536, 3072, or more wells. In some embodiments, a container comprises a test compound and cells are added to the container. In some embodiments, the container comprises the cell and the test compound is added to the container. In some embodiments, the level of Syp/Syb complex is determined in the same container as was used for the contacting step. Microtiter and multi-well plates suitable for use in assays of the invention include commercially available varieties known in the art, such as those sold by BioRad Laboratories (Hercules, Calif.), Life Technologies (Carlsbad, Calif.), Sigma-Aldrich (St. Louis, Mo.), Thermo Fisher Scientific (Rochester, N.Y.), and others. In some embodiments, the plate comprises wells comprising one or more transparent or translucent surfaces, such as a bottom surface, a wall, a top surface, or a combination thereof In some embodiments, one or more surfaces of a well in a sample array comprise a material that selectively allows transmission of one or more wavelengths of light. In some embodiments, one or more surfaces of a well in a sample array comprise a material that selectively blocks transmission of one or more wavelengths of light. In some embodiments, cells added to the sample array are allowed to adhere and/or grow prior to subjecting the sample to an assay. Cells may adhere to any surface or a selected surface of a well. Cells in the sample array can be subjected to an assay as adherent cells, cells in suspension, or a combination of these. In some embodiments, the sample array is sealed throughout an assay. In some embodiments, the contents of the wells are manipulated at one or more points during an assay, such as by the removal of well contents and/or addition of reagents.

The step determining a level of Syp/Syb complex may be performed using an optical system capable of detecting and/or monitoring the results or the progress of reactions taking place in wells of multi-well plates. Typically, such optical system achieves these functions by first optically exciting the reactants, followed by collecting and analyzing the optical signals from the reactants in the micro wells. In one embodiment, the optical system comprises an optical excitation element, an optional optical transmission element, and a photon-sensing element. The optical system may also comprise an optional optical selection element.

The optical excitation element acts as the source of excitation beams used to optically excite the contents of the micro wells, such as a fluorescent label. This element encompasses a wide range of optical sources that generate light beams of different wavelengths, intensities and/or coherent properties. Representative examples of such optical excitation sources include, but are not limited to, lasers, light-emitting diodes (LED), ultra-violet light bulbs, and/or white light sources.

An optical transmission element may be used to serve one or both of two functions. First, it may collect and/or direct the optical excitation sources to the contents of the wells. Second, it may transmit and/or direct optical signals emitted from the contents of the wells of the chips to the photon-sensing element. The optical transmission element encompasses a variety of optical devices that channel light from one location to another. Non-limiting examples of such optical transmission devices include optical fibers, optical multiplexers (MUX) and de-multiplexers (DE-MUX), diffraction gratings, arrayed waveguide gratings (AWG), optical switches, mirrors, lenses, collimators, and any other devices that guide the transmission of light through proper refractive indices and geometries.

The photon-sensing element detects the spectra of the optical signals coming from the reactants inside the micro wells. Suitable photon-sensing element can detect the intensity of an optical signal at a given wavelength, and preferably can simultaneously measure the intensities of optical signals across a range of wavelengths. Preferably the element may also provide spectrum data analyses to show the spectrum peak wavelength, spectrum peak width, and background spectrum noise measurements. Representative examples of suitable photon-sensing element for the present invention are avalanche photo diodes (APD), charge-coupled devices (CCD), electron-multiplying charge-coupled device (EMCCD), photo-multiplier tubes (PMT), photo-multiplier arrays, gate sensitive FET's, nano-tube FET's, and P-I-N diode. As used herein, CCD includes conventional CCD, electron-multiplying charge-coupled device (EMCCD) and other forms of intensified CCD.

Where desired, the optical system of the present invention can include an optical selection element. This element selects and/or refines the optical properties of the excitation beams before they reach the reactants contained in the micro wells. The optical selection element can also be employed to select and/or refine the optical signals coming from the reactants in the micro-wells before the signals reach the photon-sensing element. Suitable optical selection element can select and modify a wide range of optical properties, including but not limited to, polarization, optical intensities, wavelengths, phase differences among multiple optical beams, time delay among multiple optical beams. Representative examples of such optical selection elements are polarization filters, optical attenuators, wavelength filters (low-pass, band-pass or high-pass), wave-plates and delay lines.

In some embodiments, the optical system is employed to stimulate and detect fluorescence resonance energy transfer (FRET). For example, one member of Syp/Syb complex labeled with a first fluorescent tag is excited at a selected wavelength by the optical excitation element, and fluorescence by a second fluorescent tag associated with a second member of Syp/Syb complex is detected by the photon-sensing element. The two tags are members of a FRET pair, many examples of which are known in the art. In one embodiment, the first fluorescent tag is CFP and the second fluorescent tag is YFP. In general, a decrease in the intensity of photon emission by the second fluorescent tag is indicative of reduce FRET and a reduced level of Syp/Syb complex.

Figure 4:
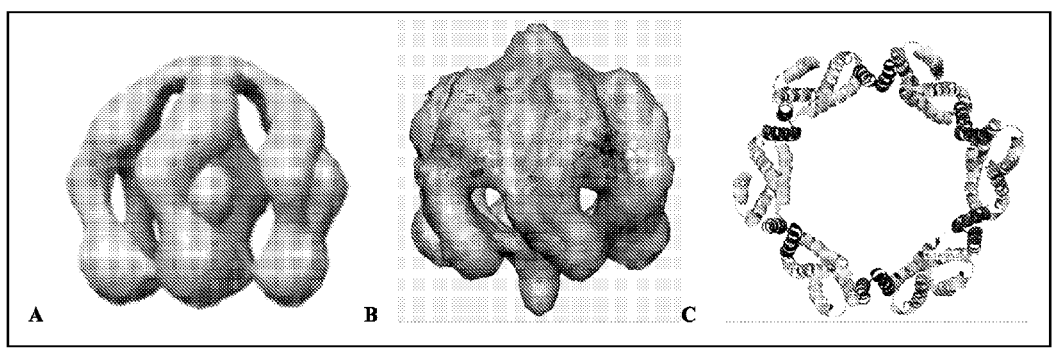
FIG. 4 shows illustrative structures of Syp and of a Syp/Syb complex useful for in-silico drug screening.

In some embodiments, candidate test compounds are selected based on x-ray crystallographic structures or molecular models of the Syp/Syb complex. An illustration of the structures Syp, Syp/Syb complex, and a molecular model of the Syp/Syb complex are provided in FIG. 4A, FIG. 4B, and FIG. 4C, respectively. In various embodiments, candidate test compounds are evaluated by in silico screening methods. Such methods may include docking of a test compound in a molecular model of the Syp/Syb complex to evaluate binding and/or modulatory potential. In various embodiments, the molecular model of the Syp/Syb complex with or without the test compound is an ab initio model. In various embodiments, the complex is modeled in a membrane environment. In various embodiments, the in silico screening methods include a model based on electron microscopy (EM). EM models may be low resolution or high resolution. For example, in various embodiments, the model based on electron microscopy has resolution better than about 20 angstroms, better than about 15 angstroms, better than about 10 angstroms, better than 5 angstroms, and the like.

In one aspect, the invention provides a compound identified using an assay of the invention. In one embodiment, the compound comprises a modulator that inhibits the disruption by Aβ of a complex comprising synaptophysin and/or synaptobrevin in an amount sufficient to treat AD. In some embodiments, the compound is selected from the group consisting of compounds described herein.

In one aspect, an assay is provided for evaluating the effectiveness of a putatitve modulator of E3 and/or SIAH-1/2 in stabilizing or inhibiting the degradation of synaptophysin for the purpose of developing a lead compound for treatment or diagnosis of Alzheimer's Disease. Accordingly, in various embodiments the putative modulator is added to a cell assay in the presence of synaptophysin, and optionally a control protein such as actin. The cells are incubated and the amount of synaptophysin remaining after incubation is determined. Assays may include the addition of Aβ1-42. The putative modulators may be peptides, such as peptide fragments from synaptophysin, or may be small molecules with structural elements derived from peptides.

In one aspect, the invention provides a kit. In some embodiments, the kit comprises one or more compounds as described herein. In some embodiments, the kit comprises one or more compounds, reagents, or systems for the performance of an assay and/or method of the invention. Reagents and compounds may be provided in any suitable container. Kits may further comprise instructions for the use of reagents, compounds, and/or systems included as part of the kit.

Diagnostics

The invention further contemplates a diagnostic kit and method for AD which comprises measuring the levels of Syp and the Syp/Syb complex. In various embodiments, the detection method is an indicator of the pathological state of AD, and may comprise the steps of: detecting qualitatively or quantitatively the amount of Syp/Syb complex in a sample from a putative patient. In various embodiments, a diagnostic kit for diagnosing AD comprises a detection means for qualitatively or quantitatively detecting Syp and/or Syp/Syb complex in a sample from a putative patient, as an indicator of the pathological state of AD. In various embodiments, a diagnostic marker for diagnosing Alzheimer's disease comprises Syp and/or Syp/Syb complex as an indicator in a blood sample or other type of biological sample. The indicator of AD may refer to an indicator relating to the pathology of AD, which includes for example, the onset of AD, senile dementia of AD type, and the like. Thus, the pathological indicator for AD includes for example, an indicator for the prediction of the degree of risk for onset of senile dementia, the prediction and/or diagnosis of early stage AD, the estimation of the degree of brain dysfunction, clinical comprehension, the prediction of the course of the disease, the observation and/or evaluation of therapeutic results, prognosis prediction, and the like. In various embodiments, the diagnostic marker, in addition to reflecting the clinical state of AD, is both highly sensitive and highly specific to the detection of AD.

Diagnostic kits may comprise a carrier, package or container that is compartmentalized to receive one or more containers such as vials, tubes, and the like, each of the one or more containers comprising one of the separate elements to be used in the method, such as an antibody, anti-idiotypic antibody or composition of the invention. The kit of the invention will typically comprise the container described above and one or more other containers comprising materials desirable from a commercial and user standpoint, including buffers, diluents, filters, needles, syringes, and package inserts with instructions for use. In addition, a label can be provided on the container to indicate that the composition is used for a specific therapeutic or diagnostic application, and can also indicate directions for use. Directions and or other information can also be included on an insert which is included with the kit. In various embodiments, the diagnostic kit includes an antibody to Syp and/or Syp/Syb complex. The antibody may be labeled or unlabeled. In various embodiments, the diagnostic kit includes an enzyme-linked immunosorbent assay (ELISA). Fragments of antibodies are also included. As an antibody fragment, an F(ab')2 fragment, an Fab' fragment and the like, may be exemplified. Additionally, in a case where the antibody is a monoclonal antibody, the globulin type is not specifically limited in any way. For example, IgG, IgM, IgA, IgE, IgD, and the like, may be provided. Moreover, the monoclonal antibody may also be a humanized antibody.

Marketing Of Modulators

Methods according to the invention are also directed to marketing the target modulators identified according to the methods of the invention. For example, in one embodiment, the invention is directed to a method of evaluating the commercial market for a target modulator. Such methods may include producing a target modulator as described herein, making sample amounts of the target modulator available for no cost or for minimal cost, and measuring the number of requests for the target modulator over a period of time. Advantages of making a target modulator available in this manner may include an improved calculation of the future supplies needed and/or future demand by paying customers. Alternatively, providing a target modulator at no cost or minimal cost initially may induce interest in the target modulator and the discovery of favorable characteristics for the modulator that spur future sales. Minimal cost may include a price that is approximately the cost of production with essentially no profit involved. In various embodiments, the minimal cost may be about 10%, about 20%, about 30%, about 40%, about 50%, about 60%, or about 70% of the price of a competitor's product.

EXAMPLES

General:

Animals: All animal procedures were carried out in accordance with protocols approved by the IACUC at CU Boulder and the Animal Welfare Assurance filed with OLAW. B6 mice (Jax) were used as WT in all experiments. SYP -/- animals (Eshkind and Leube, 1995b) were a gift of R. Leube at RWTH Aachen University.

Synaptosomes: Whole brains were obtained from age-matched female B6 and SYP -/- adults. Brains were homogenized 13 strokes on ice in 4 mL of sucrose buffer (10 mM HEPES pH 7.4, 320 mM sucrose, 2 mM EGTA, 2mM EDTA) with protease inhibitor cocktail (Roche, Basel, Switzerland) and homogenates were cleared at 4 ° C. at 1000 g for 10 minutes. Synaptosomes were pelleted at 10,000 g at 4° C. for 20 minutes, resuspended in buffer (25 mM HEPES pH 7.4, 150 mM NaCl, 10 mM $MgCl_2$, 1 mM EDTA, 1% glycerol) and total protein was quantified with the Pierce 660 nM Protein Assay kit.

Aβ42 Column: AminoLink resin (Pierce, Rockford, Ill.) was functionalized according to manufacturer specifications with BioPure™ recombinant Aβ42 or scrambled Aβ42

(AmideBio, Boulder, Colo.). Whole brain synaptosomes from B6 or SYP -/- mice were applied to column overnight at 4° C. in IP buffer (25 mM HEPES pH 7.4, 150 mM NaCl, 10 mM MgCl$_2$, 1 mM EDTA, 1% glycerol, 0.5% NP-40) with protease inhibitor cocktail (Roche). Beads were washed three times and bound material was eluted at 95° C. in 2X SDS sample buffer.

Antibodies: Antibodies were obtained from Synaptic Systems, Goettingen, Germany (SYP, VAMP2, MAP2), Santa Cruz Biotechnology, Santa Cruz, Calif. (synaptoporin, synaptogyrinl), and Pierce (synaptogyrinl), Covance Research Products, Inc. (Aβ42, 4G8 and 6E10) and Noyus Biologicals (Aβ42, NB300-226).

Surface Plasmon Resonance: Binding studies were performed on a Biacore 3000 or a BiOptix 404 pi, with similar results. For the Biacore, a CM5 chip was used and for the BiOptix instrument, a CMV150 chip was employed. BioPure™ recombinant Aβ42, scrambled Aβ42, or Aβ42-1 (AmideBio, Boulder, Colo.) was dissolved to 0.1 mM in 10 mM sodium hydroxide, and diluted to 1 uM in 10 mM sodium acetate pH 4.0 immediately prior to immobilization using EDC-NHS chemistry. Recombinant human SYP, containing a His(6)-tag expressed in insect cells, was a gift of J. Mapes and A. DeFazio at CU Boulder. Bovine serum albumin (Sigma, St. Louis, Mo.), Interleukin 1 receptor antagonist (gift of Synergen, Inc., Boulder, Colo.), and SLC35F1 (gift of G. Chang, UCSD) were used as control proteins. Binding at a flow rate of 20 µl/min was in 0.15M sodium chloride, 0.03M sodium HEPES, pH 7.4, 0.009% Fos-choline 14 (Anatrace, Santa Clara, Calif.) for all samples.

Densitometry: Western blot values of co-precipitated protein were normalized to levels of recovered bait protein and shown as a ratio over samples treated with scrambled Aβ42.

Cell Culture: Cortical neurons were prepared as described previously (Beaudoin et al., 2012) and plated at high density (~5000 cells/mm$^2$) to ensure physiologically relevant synaptic connections. Imaging was performed at 12-15 DIV. Neurons were treated with 10 to 15 nM Aβ42 or scrambled peptide (R Peptide, Bogart, Georgia or AmideBio, Boulder, Colo.) 24 hours prior to imaging by dissolving the peptide at 1 mg/ml in 10 mM NaOH, followed by bath sonication and centrifugation at 13,000 rpm for 5 minutes. The concentration was then determined using a Nanodrop at 280 nm and cross validated using both a BCA assay and SDS-PAGE as described in AmideBio application note 101 and SOP 212. Cells were treated within 1 hour of sample preparation by removal of 1 ml of conditioned media, addition of peptide to the conditioned media and then replacement of the mixture to the culture dish. No difference was observed between scrambled peptide and vehicle.

FM 1-43 Assay: Neurons were labeled with 10 µM FM 1-43 (Invitrogen, Carlsbad, Calif.) in stimulating buffer (25 mM HEPES pH 7.4, 59 mM NaCl, 70 mM KCl, 2 mM CaCl$_2$, 1 mM MgCl$_2$, 30 mM glucose) for 2 minutes at 37° C. followed by washing in a calcium-depleted buffer (25 mM HEPES pH 7.4, 124 mM NaCl, 5 mM KCl, 0.2 mM CaCl$_2$, 5 mM MgCl$_2$, 30 mM glucose) to prevent release of labeled vesicles prior to assay. Cultures were depolarized under profusion with stimulating buffer and imaged for 60 seconds after onset of release. Synaptic puncta were identified in ImageJ(Schneider et al., 2012) by making a max projection of the video, background subtraction of 0.5*mean pixel intensity and finding local maxima on a 10 px (~650 nm) radius with the NEMO-derived(Iannuccelli et al., 2010) ImageJ plugin 3D Fast Filter. These maps were enlarged over a 5 px radius and mean grey value of each punctum was plotted against time. Each unloading curve was fitted to an exponential decay equation of the form $$f(t) = f_0 \cdot e^{(\frac{-1}{\tau})t} + c$$

to determine a time constant, τ, to represent the kinetics of release at each synapse. These data were filtered for particles whose behavior poorly fit an exponential model ($R^2$<0.95) and the data presented was trimmed to values of τ between 0 and 500 seconds, although a small number of extremely slow decay events were observed. The remaining values were sorted into 5 second bins and displayed as a histogram. Each bin represents the sum of all biological replicates at each t value normalized to the mode of each distribution.

Hippocampal slice preparation and electrophysiology: Hippocampal slices (400 µm) were prepared from mice 2-4 months of age using a vibratome as described previously (Hu et al., 2006). The slices were maintained at room temperature in a submersion chamber with artificial CSF containing the following (in mm): 125 NaCl, 2.5 KCl, 2 CaCl2, 1 MgCl2, 1.25 NaH2PO4, 24 NaHCO3, and 15 glucose, bubbled with 95% O2/5% CO2. Slices were incubated for at least 2 h before removal for experiments. For electrophysiology experiments, slices were transferred to recording chambers (preheated to 32° C.) where they were superfused with oxygenated ACSF. Monophasic, constant-current stimuli (100 µs) were delivered with a bipolar silver electrode placed in the stratum radiatum of area CA3, and the field EPSPs (fEPSPs) were recorded in the stratum radiatum of area CA1 with electrodes filled with ACSF (resistance, 2-4 me). Baseline fEPSPs were monitored by delivering stimuli at 0.033 Hz. fEPSPs were acquired, and amplitudes and maximum initial slopes measured, using pClamp 10 (Molecular Devices). LTP was induced with a high-frequency stimulation (HFS) protocol consisting of two is long 100 Hz trains, separated by 60 s, delivered at 70-80% of the intensity that evoked spiked fEPSPs (Tsokas et al., 2007). Incubation of hippocampal slices with Aβ42 was performed in either recording chambers or maintenance chambers as needed. The final concentrations of Aβ42 stock was prepared in DMSO and stored at −20° C. for at least 24 h before use at a final concentration of 500 nm.

Alignments: Human sequences of SYP and homologs were obtained from the Uniprot database (uniprot.org). Paralog tree was produced with the simple analysis tool from phylogeny. ft.

Immunoprecipitation: Five µg of precipitating antibody was bound to PureProteome protein A magnetic beads (Millipore, Billerica, Mass.) in IP buffer (25 mM HEPES pH 7.4, 150 mM NaCl, 10 mM MgCl$_2$, 1 mM EDTA, 1% glycerol, 0.5% NP-40) for 10 minutes and the beads were washed. Whole brain synaptosomes were applied in IP buffer with protease inhibitor cocktail (Roche) overnight at 4° C. Beads were washed thrice in IP buffer and bound material was eluted at 95° C. in 2X SDS sample buffer.

Example 1

Analysis of Levels of Syp/Syb Complex in Culture and in AD Patients

In this example, levels of Syp/Syb complex are determined for cultured neurons and for tissues extracted from AD patients. For evaluation in cell culture, murine hippocampal neurons were incubated overnight with 50 nM Aβ

(1-42). Proteins were extracted using standard techniques. Samples were immunoprecipitated using 0.3% TX100 at 4° C. for 1 hour in 10 mM Tris-HCL and anti-Syp antibody (Synaptic Systems). Protein-G beads were added an incubated for 1 hour. The beads were isolated by low speed centrifugation at 1000 g and SDS-PAGE buffer was added, the samples boiled, and loaded on a PAGE gel. Standard SDS-PAGE analysis and subsequent immunoblotting were performed and both Syp and Syb were quantified using anti-Syp and anti-Syb antibodies and results were normalized using a standard curve. Results are shown in FIG. 1A, and are presented as a ratio of Syp to Syb. The results demonstrate a reduction in the amount of Syp/Syb complex of approximately 50% in the Aβ treated cells relative to the untreated control cells. For evaluation in AD patient samples, synaptic proteins from AD patients, patients with pre-Alzheimer's disease (pAD), and control subjects not suffering from AD were isolated using standard methods. Levels of Syp and Syb were determined by immunoprecipitation and blot as above. Results are shown in FIG. 1B, and are presented as a ratio of Syp to Syb. The results demonstrate a progressive reduction in Syp/Syb complex with progression of AD.

Example 2

Analysis of Levels of Syp/Syb Complex in AD Patients

Hippocampal (primarily CA1) tissue from Alzheimer's disease patients classified using standard Braak & Braak and CERAD criteria with no evidence of concomitant processes can be extracted using a 2 or 4 mm Acu-Punch. Aged matched controls can be similarly extracted. Samples can be homogenized in a Brinkman Polytron in cold 10 mM Tris-HCL (pH 7.4) containing 10% (wt/vol) sucrose and protease inhibitor cocktail. Crude homogenates can be centrifuged for 10 min at 1000 g and the supernatant centrifuged at 100 kg for 20 min. The crude pellet from the 100 kg spin can be solubilized using 0.3% TX100 at 4° C. for 1 hour in 10 mM Tris-HCL and anti-Syp antibody (Synaptic Systems). Protein-G beads can be added and incubated for 1 hour. The beads can then be isolated by low speed centrifugation at 1000 g, SDS-PAGE buffer added, and the samples boiled and loaded on the PAGE gel. Standard SDS-PAGE analysis can then be performed as is Example 1, followed by quantification using anti-Syp and anti-Syb antibodies that have been normalized using a standard curve. The complex can also be analyzed using MudPIT (multi-dimensional protein identification technology). Samples can be treated immunoprecipitated as above and then SDS can be removed via solvent precipitation and then analyzed on an Orbi-Trap LC-MS/MS.

Example 3

Figure 2:
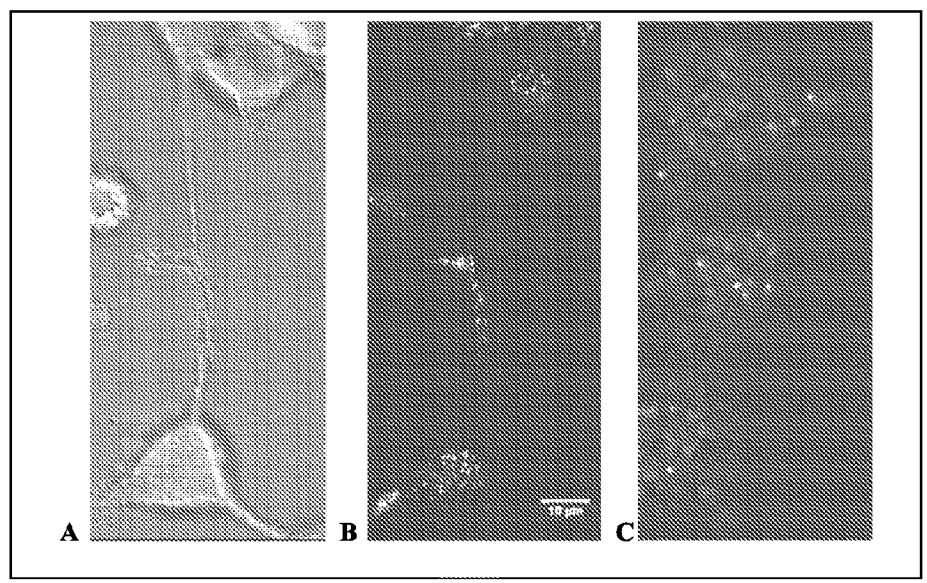
FIG. 2 shows a differential interference contrast images (A), a FRET overview image (B), and a FRET heat map image (C) of cells useful in an assay of the invention.

Generation of Cells for FRET Based Assay for Determining the Level of Syp/Syb Complex PC12 cells were stably transfected with fluorescent chimeras of Syp and Syb. The chimeras were Syb-CFP and Syp-YFP fusion proteins. Transfected cells were incubated in 100 ng/mL media to induce differentiation. Cells were viewed under CFP, YFP, and FRET filter sets. Differential Interference Contrast (DIC) images were also collected. DIC, FRET overview, and FRET heat map images of selected regions showing FRET puncta are illustrated in FIG. 2A, FIG. 2B, and FIG. 2C, respectively.

Example 4

Assay for Screening Compounds for the Treatment of AD

Transgenic PC12 cells expressing labeled Syp and Syb proteins can be used in an assay for the detection of stabilization of Syp/Syb complex in the presence of a disruptor, such as Aβ. Multiple compounds can be tested simultaneously in a multi-well format. For example, 46 compounds can be tested in cells distributed among all wells of a 96-well plate, two wells per compound, with the 47$^{th}$ pair of wells used as an untreated control pair, and the 48$^{th}$ pair of wells receiving no test compound for use as a disruptor-treated control pair. Readings can be averaged between well pairs. All cells can be treated with Aβ, for example, at 50 nM as in Example 1, except for the untreated control cells. All cells can then be contacted with their respective test compound. FRET fluorescence can then be measured using a fluorescent microplate reader. Treatment with Aβ will disrupt the Syp/Syb complex, and result in a decrease in FRET fluorescence relative to the untreated control. Fluorescence intensity from wells containing cells contacted with test compounds can then be compared to the controls. Test compounds with higher FRET fluorescence relative to the disruptor-only control can then be identified as compounds that inhibit disruption by Aβ, and can thus be identified as compounds for the treatment of AD.

Example 5

Assay for Validating Identified AD Therapeutic Compounds

Figure 3:
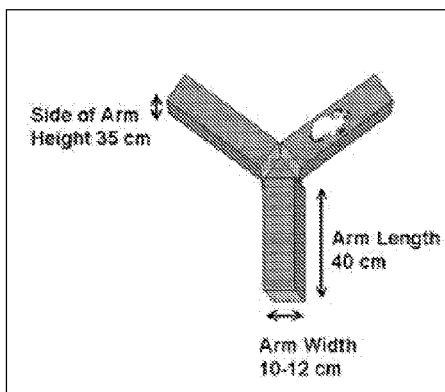
FIG. 3 shows a sample test of mice useful in evaluating compounds of the invention (A), and sample results (B).
Figure 3:
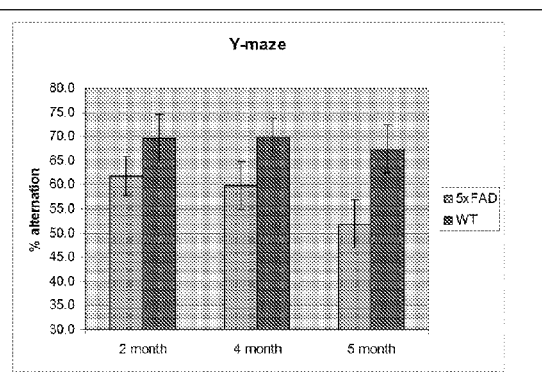

Compounds identified by an assay such as described in Example 4 can be validated in animal models of AD before testing in humans. Two such mouse models include 5XFAD and 3STG. A cognitive behavior assay can be used to compare the behaviors of matched treated and untreated mice. One such assay is the Y-maze test, used to determine the navigation behaviors of mice. Mice are placed in a Y-shaped maze for 5 to 10 minutes, and arm entries are sequentially scored so that the total number of arm entries, as well as the sequence of entries, are recorded. Data are analyzed to determine the number of arm entries without repetition. Success in this test is indicated by a high rate of alternation in normal mice, and in successfully treated 5XFAD mice, indicating that the animals can remember which are was entered last. A schematic diagram of the test and typical data observed in a comparison of the behavior of normal and 5XFAD mice are presented in FIG. 3.

Example 6

Assay for Protection of Synaptophysin Degradation by Peptide-Based Inhibitors

Differentiated PC12 cells are incubated for 24 hrs with 200 nM Aβ1-42. Cells are then incubated for 8 h in the presence or absence of SIAH-1/2 binding inhibitors as shown in Table 1. Cells are then lysed, and an equal amount of protein (BCA assay) from each lysate is analyzed by immunoblotting for both synaptophysin and actin as in internal control. The amount of synaptophysin is determined using ImageJ and normalized to the amount of actin. Peptide inhibitors are based upon the SIAH-1/2 binding domain of human synaptophysin comprising residues 277-307 and the sequence DYGQPAGSGGSGYGPQGDYGQQGYGPQ-GAPT (SEQ ID NO: 22) with the observed repeat motif D-YG(QP or PQ or QQ)GA (SEQ ID NO: 23-28).

TABLE 2

Examples of SIAH-1/2 binding inhibitors

| SEQ ID NO: 23 | DYGQQGYGPQG |
|---|---|
| SEQ ID NO: 24 | YGPQGDYGQQG |
| SEQ ID NO: 25 | DYGQPADYGQQG |
| SEQ ID NO: 26 | DYGQPAYGPQG |
| SEQ ID NO: 27 | DYGQQGYGPQG |
| SEQ ID NO: 28 | YGPQGDYGQQG |

Example 7

Study to Show that Aβ42 Directly Binds Synaptophysin in a Cholesterol-Dependent Manner.

Figure 6A:
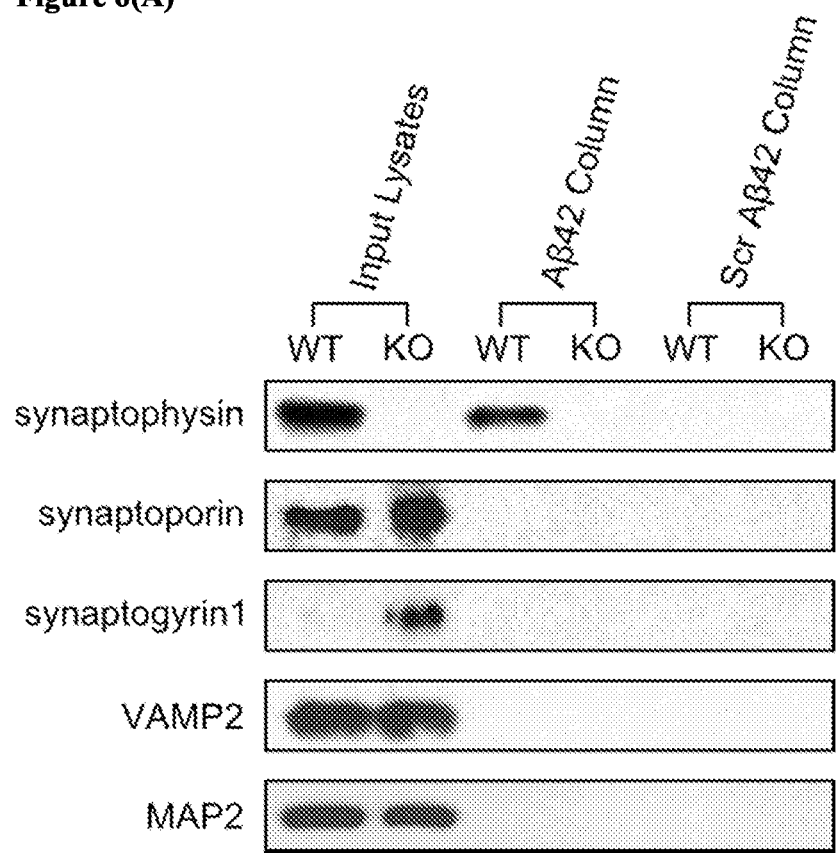
FIG. 6(A) shows western blot for synaptic proteins that bind to column immobilized Aβ42 or scrambled peptide.
Figure 6B:
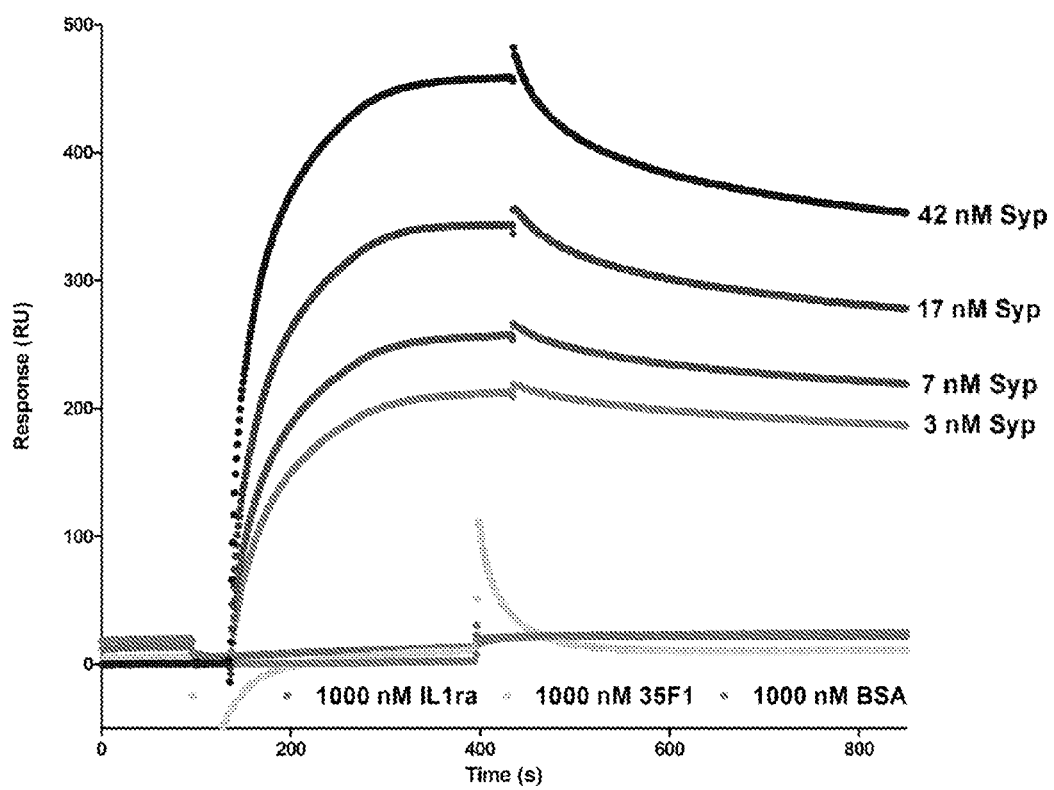
FIG. 6(B) shows SPR sensorgrams indicating binding of recombinant SYP and control proteins with similar isoelectric points (BSA, IL-lra) or similar membrane topology (SLC35F1) to Aβ42.
Figure 6C:
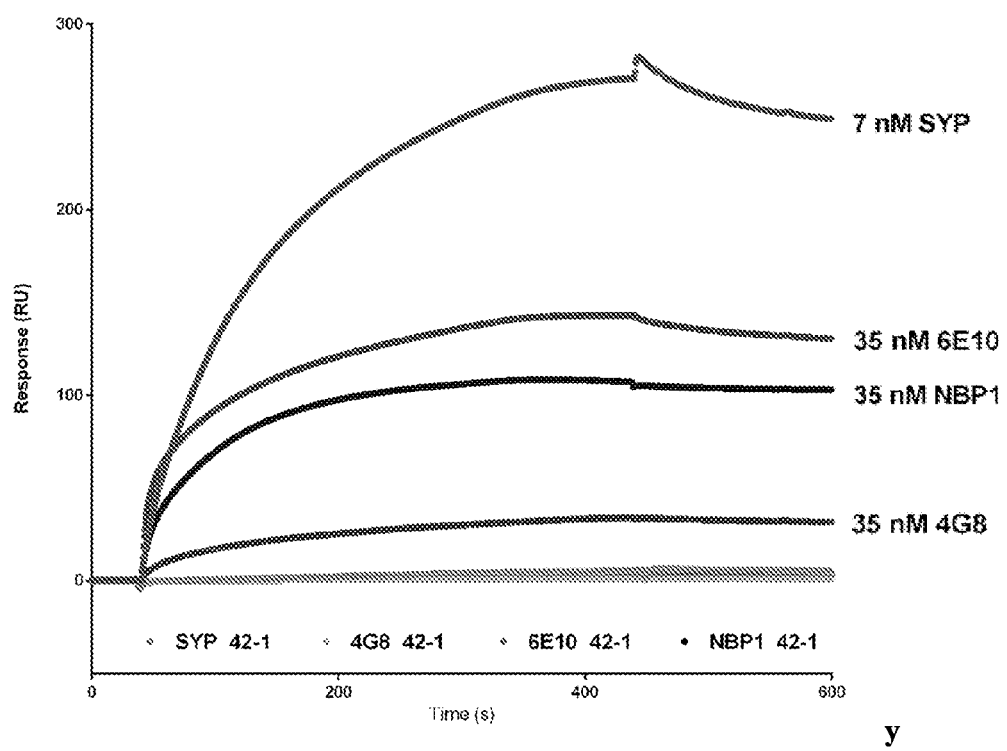
FIG. 6(C) shows SPR sensorgrams comparing SYP and anti-Aβ42 antibodies binding to both Aβ42 and Aβ42-1.

Many cellular and neurological phenotypes have been attributed to excess Aβ42 in the brain; however, it has been difficult to demonstrate that any are directly caused by the peptide. Aβ42 is highly prone to aggregation, and is the major constituent of the plaques that are the salient histopathological features of AD, yet it is the pre-fibrillar, small oligomer forms that are the toxic drivers of AD pathology (Walsh and Selkoe, 2007). To identify direct disease-relevant targets, we coupled small soluble Aβ42 oligomers to chromatography resin and tested for their ability to bind proteins from synaptosomal extracts Immobilized Aβ42 bound SYP from whole brain homogenates (FIG. 6A) and this interaction was specific to SYP, as no binding could be detected for the SYP paralogs synaptoporin (62% identity) or synaptogyrin1 (22% identity), nor for VAMP2 or the loading control, MAP2. To determine the nature of the immobilized Aβ42, and to test if SYP binding was direct, we used surface plasmon resonance (SPR) to investigate the interaction of purified human SYP as well as anti-Aβ42 antibodies to the immobilized Aβ42. We observed a remarkably robust binding of SYP to surface coupled Aβ42 over a range of protein concentrations (FIG. 6B), demonstrating that SYP can bind directly to Aβ42 in the absence of other proteins or cofactors. We also failed to observe binding of control proteins of similar membrane topology or isoelectric point. We observed an on rate of 835,507 $M^{-1}$ $sec^{-1}$ and off rate of 0.003746 $sec^{-1}$ and calculated that Aβ42 binds SYP with a $K_d$ of 4.5 nM for the SYP monomer and 750 pM for the native SYP hexamer. We did not detect any binding of SYP to immobilized, scrambled, or reverse (42-1) Aβ42 (FIG. 6B), demonstrating the specificity of this interaction. This very high affinity would provide substantial physiological binding at the low nanomolar concentrations of Aβ42 typically found in the brains of AD patients (Lue et al., 1999b). To further confirm the specificity of this binding we characterized the interaction of immobilized Aβ42 using several established anti-Aβ42 antibodies (FIG. 6C). We observed that the 6E10 antibody, which recognizes all forms of Aβ42, showed the most robust binding, whereas 4G8, which primarily recognizes the fibrillar forms of Aβ42 had the least binding. This result supports the conclusion that the surface coupled Aβ42 is primarily in the pre-fibrillar form of monomers, dimers and small oligomers. This observed affinity is tens to hundreds of times greater than previously described affinities of Aβ42 for other neuronal targets (Kam et al., 2013; Kim et al., 2013; Lauren et al., 2009), where binding affinities were determined from large oligomers and/or aggregating Aβ42 that could overestimate the affinities.

Figure 6D:
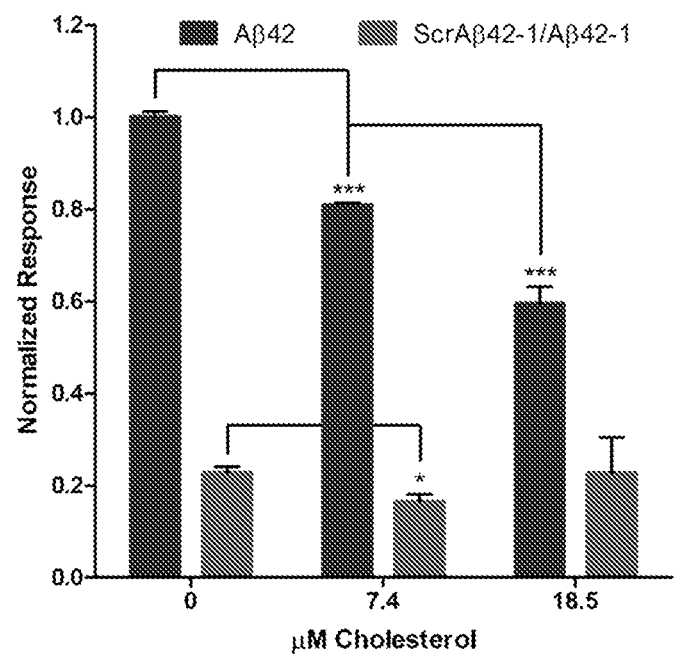
FIG. 6(D) shows normalized maximal binding of SYP to Aβ at increasing cholesterol hemi-succinate concentration. $p<0.001$ (***); $p<0.05$ (*).

The SYN/VAMP2 complex has been demonstrated to be cholesterol-dependent. We therefore asked if cholesterol inhibits the Aβ42-SYP interaction. To test if cholesterol affects the binding of Aβ42 to SYP we repeated the SPR binding experiments in the presence of increasing concentrations of the water-soluble cholesterol analog cholesterol hemisuccinate. We observed a robust concentration dependent inhibition of binding (FIG. 6D). This observation implies that cholesterol and Aβ42 binding to SYP is competitive, and further establishes a functional linkage between Aβ42 and cholesterol concentrations and the known association between AD and APP/P SEN1 or APOE4 mutations.

Example 8

Study Demonstrating that Aβ42 Disrupts the SYP/VAMP2 Complex

Figure 6E:
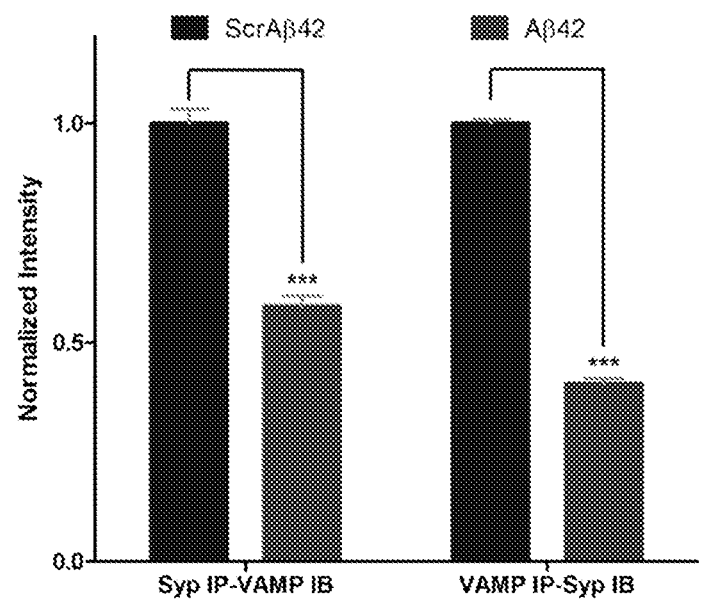
FIG. 6(E) shows ortical neurons treated with Aβ42 (blue bars) or scrambled peptide (red bars) were lysed and immunoprecipitated for SYP (left) or VAMP2 (right) and probed for the other protein. Quantification of western blots from multiple experiments; error shown as SEM (SYP IP N=3, VAMP IP N=2); p<0.001 (***).

The only physiological function directly attributed to SYP is its binding to the SNARE protein VAMP2, purportedly to down-regulate the activity of the SNARE protein (Edelmann et al., 1995). To determine if Aβ42's association with SYP impairs VAMP2 binding in vivo, we treated cultured neurons with Aβ42 peptide and performed co-immunoprecipitations. When immunoprecipitating either SYP or VAMP2 from homogenates of cultured neurons we observed that treatment with ~10 nM Aβ42 disrupted the robust association between SYP and VAMP2 by 50% or more (FIG. 6E). It has previously been reported that Aβ42 can compete SYP from immobilized VAMP2 in vitro (Russell et al., 2012). Combined with our in vivo results, this strongly suggests that VAMP2 and Aβ42 compete for a similar binding site on SYP. Furthermore, the inability to co-purify any VAMP2 along with the bound SYP on the Aβ42 column (FIG. 6A) implies that SYP association with VAMP2 and Aβ42 are mutually exclusive.

Example 9

Figure 7A:
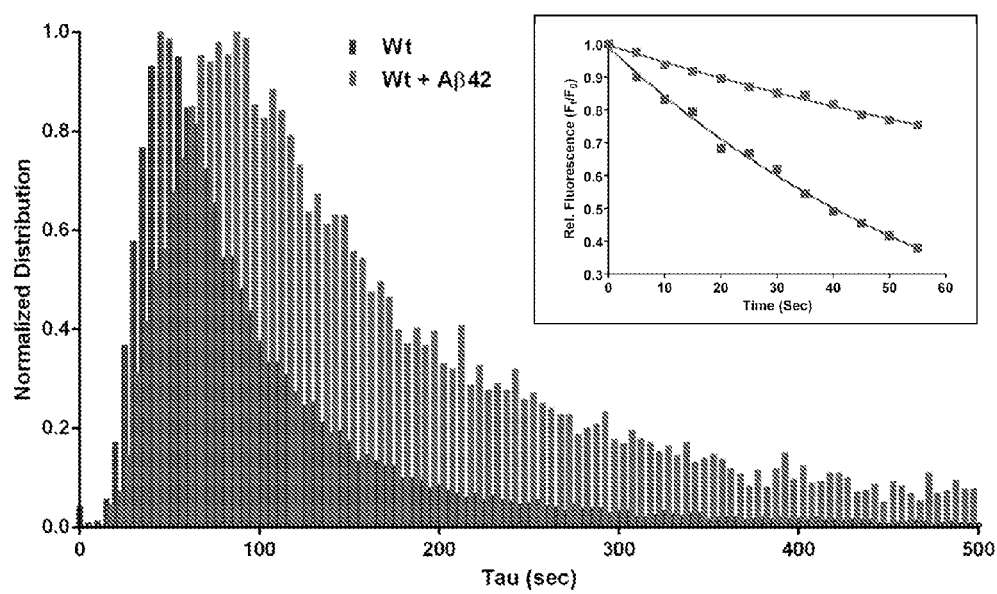
FIG. 7(A) shows distribution of kinetic time constants (τ) for all synapses observed for wild type neurons treated with Aβ42 (red, 12,364 synapses from 16 experiments) or with scrambled Aβ42 (blue, 22,996 synapses from 15 experiments). Insets show representative raw data and single exponential fits of individual synaptic release kinetics nearest the median τ value (70.5 sec for WT; 130 sec for WT+Aβ42; 66.5 sec for SYPKO; 72.5 sec for SYPKO+ Aβ42). The $R^2 > 0.98$ for all fits.
Figure 7B:
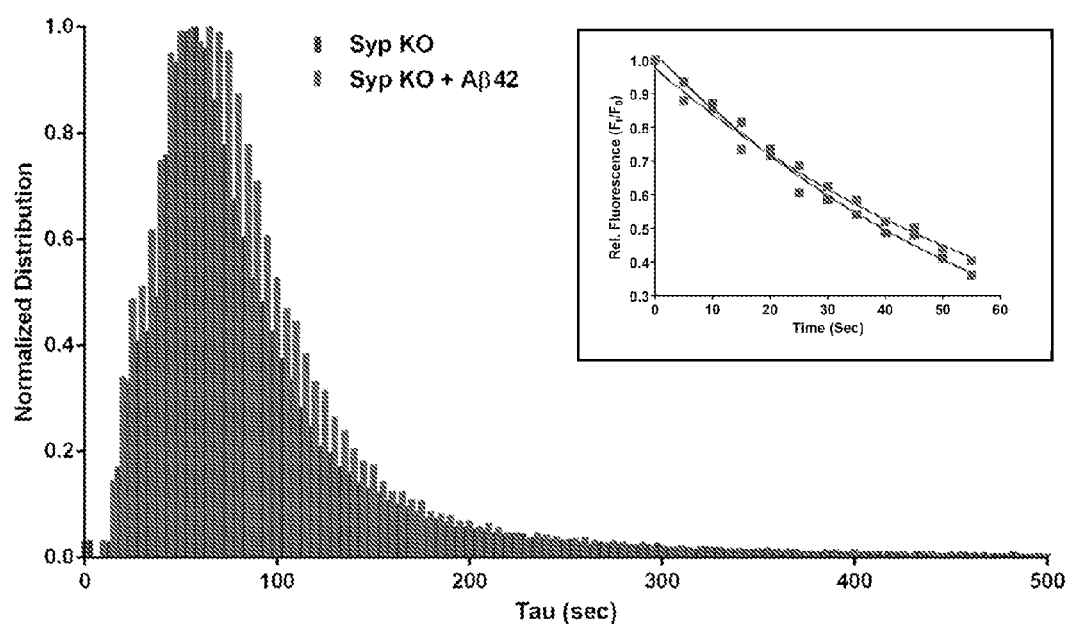
FIG. 7(B) shows distribution of kinetic time constants (τ) for all synapses observed for SYP -/- neurons treated with Aβ42 (red, 68,611 synapses from 14 experiments) or with scrambled Aβ42 (blue, 75,274 synapses from 11 experiments). Inset as above.
Figure 7C:
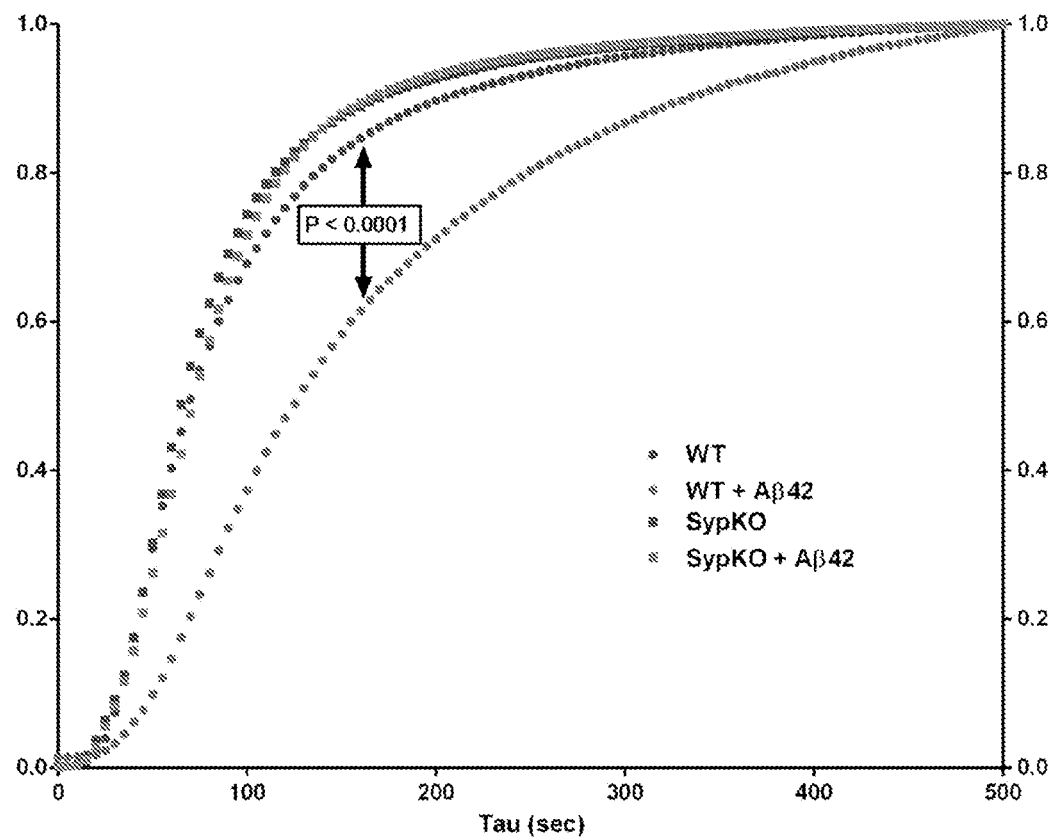
FIG. 7(C) shows cumulative distribution functions for all conditions. KS test reveals no significant difference amongst WT, SYPKO and SYPKO+Aβ42 (p>0.5) but highly significant shift from WT to WT+Aβ42 (p<0.0001).

Study Demonstrating that Aβ42 Inhibition of Synaptic Exocytosis is Synaptophysin Dependent Recent evidence has implicated SYP in SV endocytosis (Gordon et al., 2011; Kwon and Chapman, 2011), but it has long been hypothesized that SYP also regulates exocytosis by virtue of its association with the SNARE protein VAMP2 (Edelmann et al., 1995). To directly test the role of the SYP/VAMP2 interaction in exocytosis we used the lipophilic FM dye unloading method (Gaffield and Betz, 2006) to interrogate the release kinetics of more than 175,000 individual synapses from cultured cortical neurons. The change in fluorescence over time at each synapse was plotted and fit to an exponential decay described by a characteristic time constant τ (FIG. 7, insets). The t values were then sorted into bins of five seconds and represented as a histogram to visualize the full distribution of release kinetics at all synapses. We observed a fairly tight distribution of kinetic profiles with a maximum at 45 s in wild-type neurons, and this value shifted significantly to 85 s upon treatment with Aβ42 (FIG. 7A). The Aβ42-induced kinetic changes are not simply a slowed version of the control, but feature the dramatic appearance of a population of very slow (τ>400 sec.) synaptic release events not seen in the presence of control peptide. A Kolmogorov-Smirnov analysis of the entire dataset shows a very significant difference between treated and untreated, with a p<0.0001 (FIG. 7C). This result is consistent with earlier observations that Aβ42-treated neurons have reduced pools of readily releasable SVs or that SV fusion is inhibited (Moreno et al., 2009; Parodi et al., 2010). The Aβ42 dose of ~10 nM used here closely matches the observed concentrations of Aβ42 in AD brains (Lue et al., 1999a), and is many times lower than that used in previous studies (Moreno et al., 2009; Parodi et al., 2010; Russell et al., 2012), yet the magnitude of the effect we observe is similar, suggesting a threshold effect. Presumably above a certain concentration, Aβ42 either aggregates into a less active form, or the biological system becomes saturated above this threshold.

We hypothesized that Aβ42 binding to SYP and subsequent reduction of intact SYN/VAMP2 complexes are responsible for the dramatic perturbation of neurotransmitter release kinetics described above. To test this hypothesis directly we performed the FM unloading analysis in SYP -/- neurons. The loading efficiency was comparable to that observed in WT neurons but consistent with the ~10% decrease in endocytosis kinetics reported earlier (Kwon and Chapman, 2011). As predicted by other functional assays (Janz et al., 1999; McMahon et al., 1996), the knockout neurons displayed wild-type release kinetics (FIG. 7B). Remarkably however, we observed that SYP -/- neurons were insensitive to Aβ42 treatment, and we did not observe the exocytosis defects imparted by Aβ42 treatment of WT neurons. These results demonstrate that Aβ42 inhibits vesicular release by specifically interacting with SYP and disrupting normal SV fusion by slowing release kinetics. Furthermore, these data are consistent with the hypothesis that SYP enhances the kinetics of SV fusion by binding the v-SNARE VAMP2 in a clustering event to ensure multiple SNARE interactions and that this activity is one of the earliest events disrupted in AD.

Example 10

Study Demonstrating that Aβ42 Inhibition of LTP is Synaptophysin Dependent

Figure 8A:
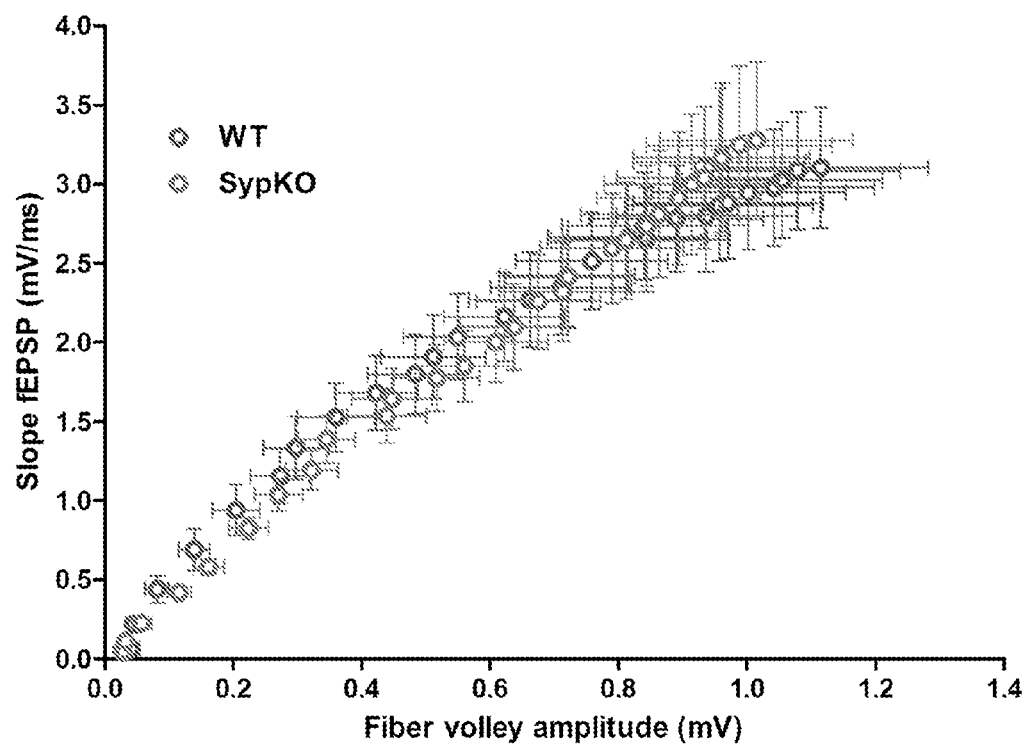
FIG. 8(A) shows that Wildtype and SypKO show similar input/output ratios demonstrating no difference in the basal neurotransmission between WT and SypKO.
Figure 8B:
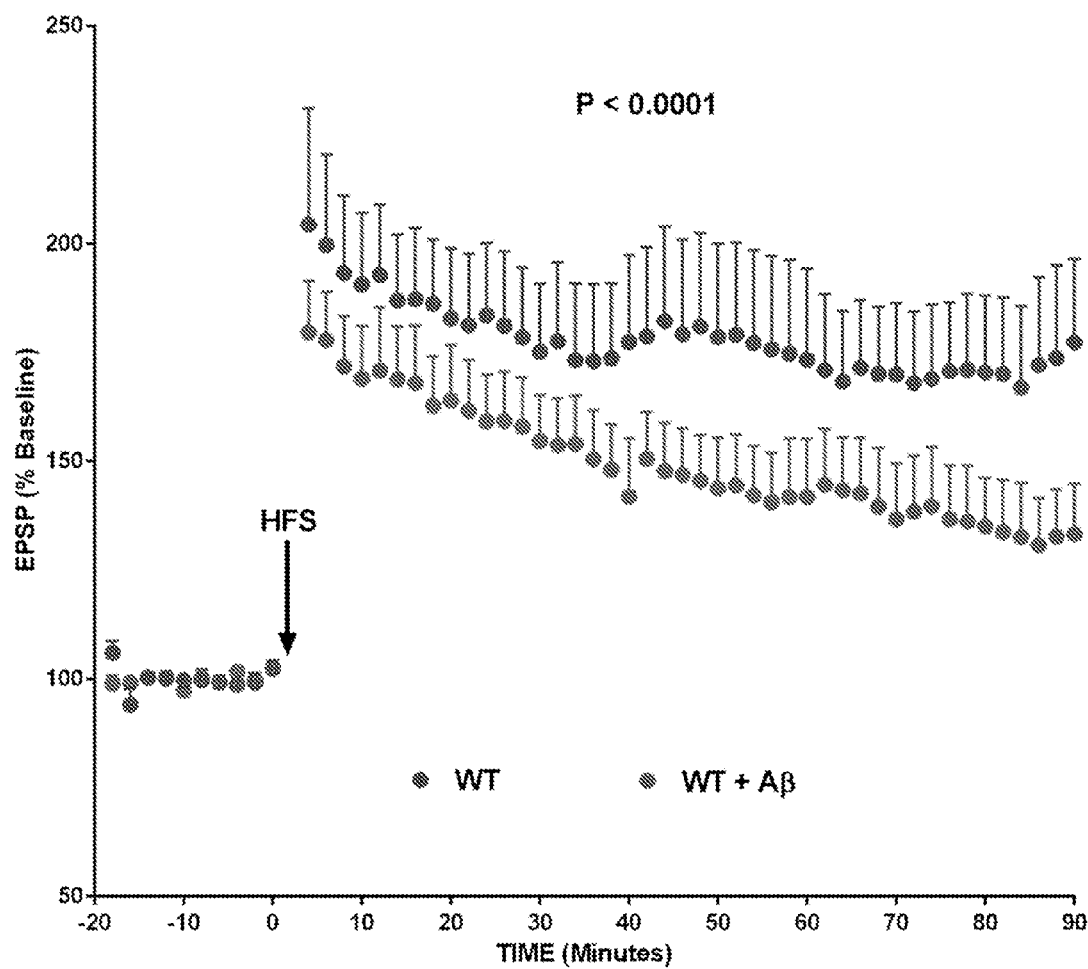
FIG. 8(B) shows LTP, as measured by the magnitude and duration of EPSPs, in WT (blue) and WT treated with Aβ42 (red), error bars are SEM. Following 4 hour treatment of slices with Aβ42 or control, EPSPs were measure before and after high frequency stimulation. The presence of Aβ42 caused a decrease in LTP as previously reported. Unpaired T-test with Welches' correction of the EPSP magnitude following the stimulation showed gave a P value less than 0.0001 between Aβ42 treated and control.
Figure 8C:
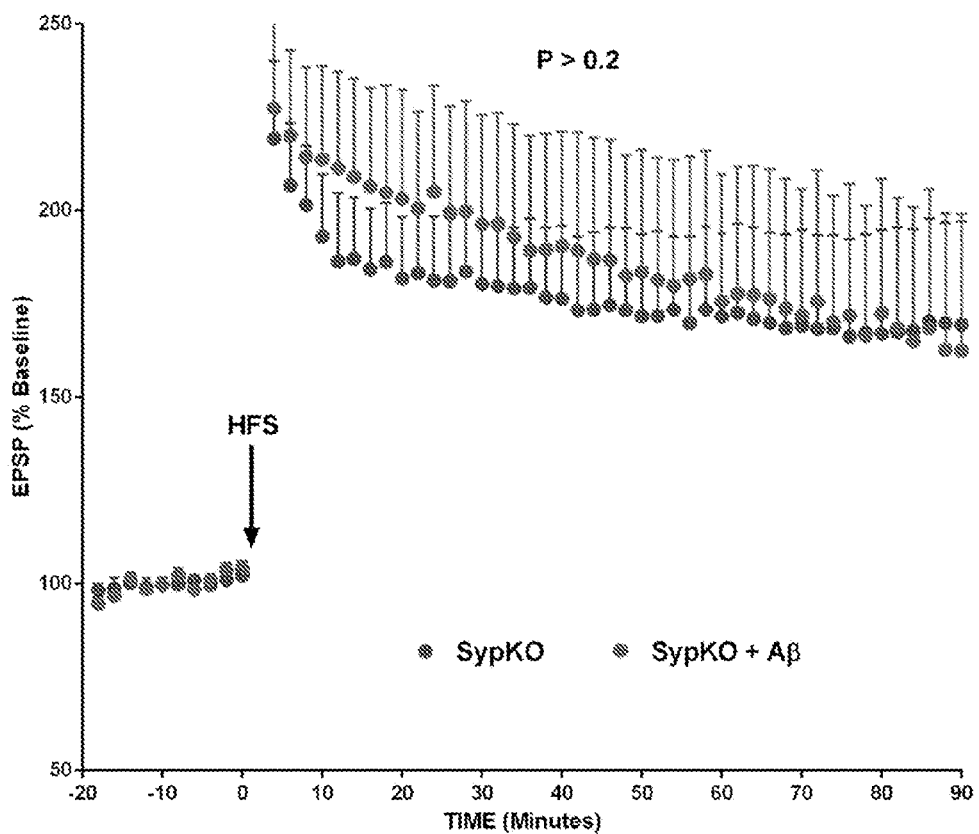
FIG. 8(C) shows LTP, as measured by the magnitude and duration of EPSPs, in SypKO and SypKO treated with Aβ42 as in A. The presence of Aβ42 failed to impair LTP as observed in WT slices and an unpaired T-test with Welches' correction of the EPSP magnitude following the stimulation showed no significant difference with a P value greater than 0.2 between Aβ42 treated and control SypKO slices.

To test the physiological consequences of SYP loss on Aβ42 synaptic inhibition we performed pair pulse studies of field excitatory postsynaptic potential (fEPSP) for WT and SYP-/- brain slices in the presence or absence of Aβ42. If SYP is a target of Aβ42 and perturbs synaptic function, then deletion of SYP should mitigate the physiological effects of Aβ42 on LTP. Aβ42 impairs hippocampal LTP and this is thought to underlie the early toxic phenomenon of AD pathology (Cleary et al., 2005; Walsh et al., 2002). To assess a direct contribution of SYP to this cellular correlate of AD pathology, we examined the effects of Aβ42 treatment on wild-type and SYP-/- hippocampal slices (FIG. 8). Slices were treated with either Aβ42 or vehicle and fEPSPs after high frequency stimulation were recorded. While Aβ42 strongly inhibited LTP in hippocampal slices from wild-type mice, in SYP-/- slices there was no significant change in the induction of LTP. These experiments demonstrate that Aβ42 inhibition of LTP is SYP dependent and consistent with our observed SYP dependent Aβ42 inhibition of release kinetics (FIG. 7). Taken together these results are in concordance with prior studies implicating presynaptic mechanisms in LTP induction (Bekkers and Stevens, 1990; Malinow and Tsien, 1990).

Example 11

Study Demonstrating that Paralogs Functionally Compensate for Loss of SYP

Figure 9A:
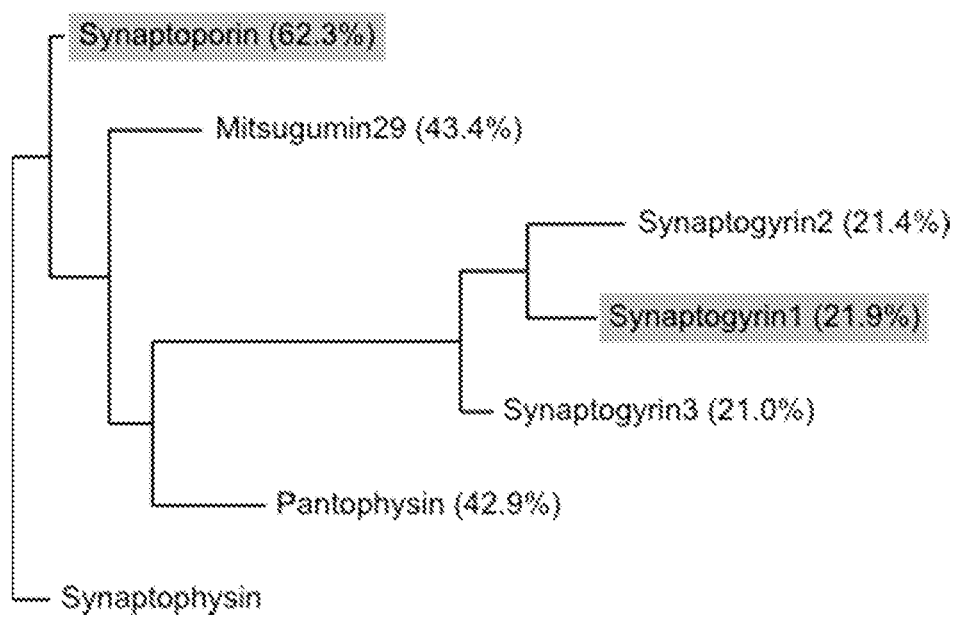
FIG. 9(A) shows the PhyML tree for SYP and all 6 neuronal paralogs, identity to SYP indicated in parentheses. Paralogs studied here are highlighted in orange.
Figure 9B:
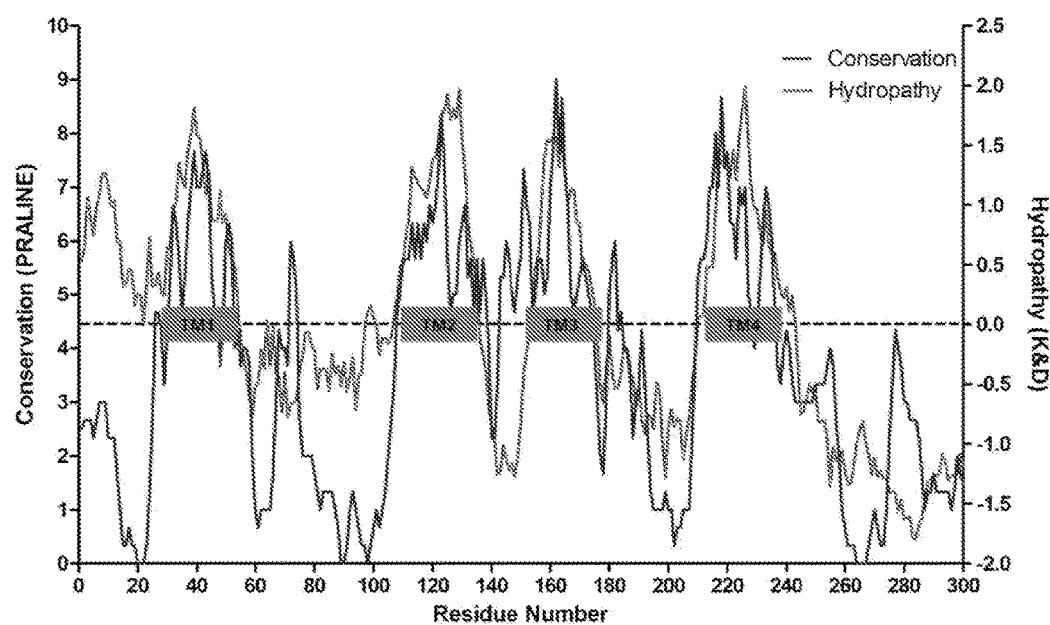
FIG. 9(B) shows the conservation score of physin family alignment (red) overlaid with SYP hydropathy score by the Kyte & Doolittle method (blue). TMDs indicated by green boxes.
Figure 9C:
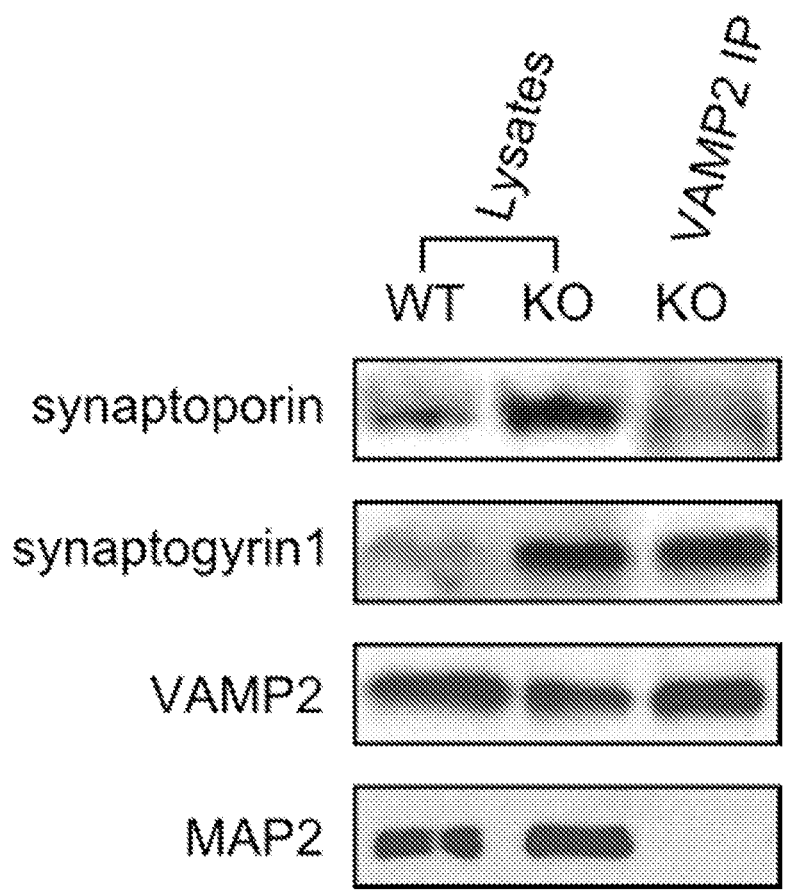
FIG. 9(C) shows the endogenous levels of synaptic proteins probed from B6 and SYP -/- whole brain synaptosomes. SYP -/- synaptosomes were immunoprecipitated with αVAMP2 and probed for synaptic proteins.
Figure 10:
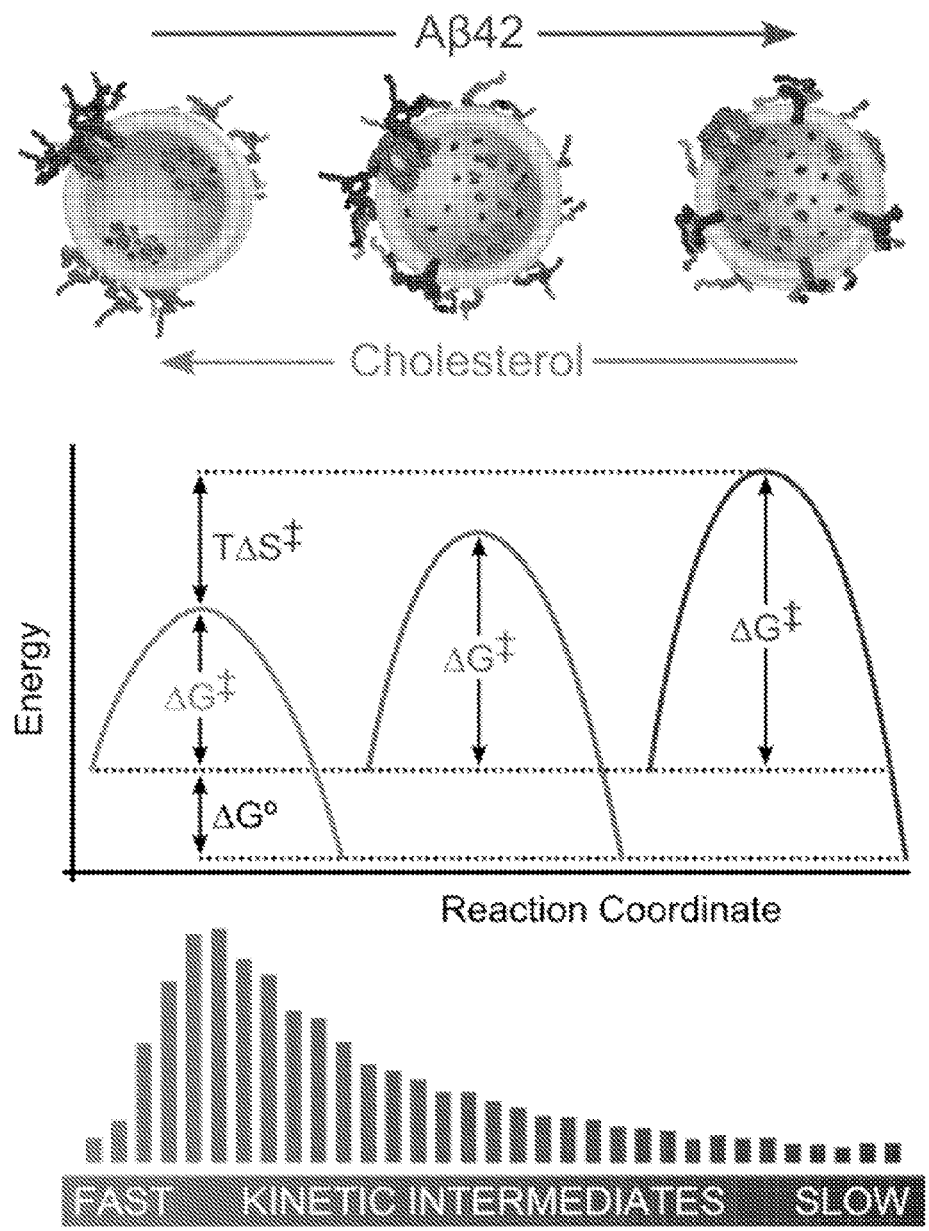
FIG. 10 shows the existence of an equilibrium between the assembled (upper left) and disassociated (upper right) forms of the SYN/VAMP2 complex with cholesterol favoring the former and Aβ42 leading to the latter. Aβ42 induces structural intermediates, partially assembled SYP/VAMP2 complexes, creating an entropic barrier (center) along the reaction coordinate, resulting in intermediate kinetic phenotypes (bottom).

At least two mammalian paralogs of SYP can functionally substitute in SYP-/- mice (Janz et al., 1999; Spiwoks-Becker et al., 2001), which explains the subtlety of the phenotypes observed. The present study as well as others (Becher et al., 1999; Gordon et al., 2011) demonstrate that the cellular function of SYP requires binding to VAMP2, which occurs via the two proteins' transmembrane domains (TMDs) (Laage and Langosch, 1997). This led us to predict that the other physin family members compensate SYP loss through a shared ability to bind VAMP2 via their respective TMDs. TMDs are not typically conserved with higher fidelity than other protein domains unless they are involved in oligomerization (Sternberg, 1990). Accordingly, one might predicted an unusually high sequence conservation of the TMDs across the physin family. Alignment of SYP with its six neuronal paralogs (FIGS. 9A) and assignment of a conservation score at each position in the alignment shows four peaks of conservation and these four peaks of conservation align directly with the four TMDs predicted by hydropathy analysis (FIG. 9B). This correspondence of conservation and hydropathy suggests that the TM domains have been more evolutionarily conserved relative to the rest of the protein. Previous studies demonstrated that the TMD of VAMP2 is dispensable for spontaneous fusion, however, the kinetics of evoked release was dramatically decreased when the SNARE TMD was replaced with a lipid anchor (Zhou et al., 2013). These results are consistent with the hypothesis that oligomerization via interactions with the conserved TMD is required for rapid physiological fusion (Arthur and Stowell, 2007). Of the mammalian SYP paralogs, SYNPR is the most similar, and an overlapping role in synaptic plasticity has been reported for synaptogyrin1 (Janz et al., 1999). We therefore evaluated these candidates for their ability to substitute for SYP in SYP-/- mice by forming a complex with VAMP2. SNG1 is expressed at very low levels in the wild-type brain, whereas SYNPR is moderately expressed. Both proteins are present at much higher levels in mice lacking SYP (FIG. 9C). This degree of developmental up-regulation would be required to replace the many copies of SYP normally complexed with VAMP2 in wild-type mice, and suggests a feedback mechanism that controls the expression levels of SYP and its paralogs to ensure the formation of a viable VAMP2 complex. Indeed, we observed significant co-immunoprecipitation of both SYNPR and SNG1 with VAMP2 in SYP-/- animals (FIG. 9C), indicating that these proteins substitute in vivo by binding VAMP2 and functionally substituting for SYP. As demonstrated above (FIG. 6A) these SYP paralogs do not bind Aβ42, which explains why knockout of SYP ameliorates the kinetic defects caused by Aβ42 treatment in wild-type neurons.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An isolated and purified peptide consisting of:
   a peptide fragment having less than about 50 amino acids, the peptide fragment having an amino acid sequence that is at least 80% homologous to a fragment of SEQ ID NO: 21, wherein the peptide fragment comprises a peptide modulator, the peptide modulator having an amino acid sequence selected from the group consisting of: SEQ ID NO: 2, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, and SEQ ID NO: 20.

2. The isolated and purified peptide of claim 1, wherein the isolated and purified peptide stabilizes the complex comprising synaptophysin, synaptobrevin, or a combination thereof.

3. The isolated and purified peptide of claim 1, wherein the isolated and purified peptide inhibits a disruptor of the complex comprising synaptophysin, synaptobrevin, or a combination thereof.

4. The isolated and purified peptide of claim 3, wherein the disruptor is an amyloid β.

5. The isolated and purified peptide of claim 4, wherein the isolated and purified peptide binds to the amyloid β.

6. The isolated and purified peptide of claim 1, wherein the isolated and purified peptide binds to the complex comprising synaptophysin, synaptobrevin, or a combination thereof.

7. The isolated and purified peptide of claim 1, wherein the isolated and purified peptide modulates a complex comprising synaptophysin, synaptobrevin, or a combination thereof.

8. A pharmaceutical composition comprising the isolated and purified peptide of claim 1 and a pharmaceutically acceptable carrier.

9. The pharmaceutical composition of claim 8, further comprising a penetration-enhancing molecule.

10. The pharmaceutical composition of claim 9, wherein the penetration-enhancing molecule is selected from the group consisting of: a humectant, urea, a glycol, propylene glycol, an alcohol, ethanol, a fatty acid, oleic acid, a surfactant, isopropyl myristate, sodium lauryl sulfate, a pyrrolidone, glycerol monolaurate, a sulfoxide, a terpene, menthol, an amine, an amide, an alkane, an alkanol, calcium carbonate, calcium phosphate, a sugar, a starch, a cellulose derivative, gelatin, a polymer, and polyethylene glycol.

11. The pharmaceutical composition of claim 8, further comprising a solubilizer.

* * * * *

SEQUENCE LISTING

<160> NUMBER OF SEQ ID NOS: 30

<210> SEQ ID NO 1
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Val Gly Asp Gly Gly Leu Phe Glu Lys Lys Leu
1               5                   10

<210> SEQ ID NO 2
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Val Gly Asp Gly Gly Met Phe Glu Lys Lys Met
1               5                   10

<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Val Gly Asp Gly Gly Leu Phe Glu Lys Lys Leu
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ile Gly Asp Gly Gly Leu Phe Glu Lys Lys Leu
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Val Gly Asp Gly Gly Asp Phe Gln Lys Lys Met
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 6

Val Gly Asp Gly Gly Val Phe Glu Thr Lys Ile
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Val Gly Asp Gly Gly Val Phe Glu Gln Lys Phe
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ile Gly Gln Gly Gly Met Phe Thr Lys Lys Leu
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ile Gly Asp Gly Gly Arg Phe Glu Arg Arg Leu
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Val Gly Asp Gly Ser Met Phe Glu Lys Lys Lys
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Val Gly Asp Gly Gly Gln Phe Glu Lys Glu Trp
1               5                   10

<210> SEQ ID NO 12

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ile Gly Asp Gly Gly Leu Phe Lys Arg Lys Tyr
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ile Gly Asp Gly Gly Ile Ile Glu Lys Glu Met
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Val Gly Asp Gly Gly Ile Ile Glu Lys Glu Met
1               5                   10

<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Val Gly Asp Gly Asp Thr Phe Glu Lys Lys Met
1               5                   10

<210> SEQ ID NO 16
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ile Gly Asp Gly Gly Val Phe Glu Thr Lys Ile
1               5                   10

<210> SEQ ID NO 17
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17
```

Val Gly Asp Gly Gly Val Phe Glu Thr Lys Ile
1               5                   10

<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Val Gly Asp Gly Gly Leu Phe Glu Ala Lys Leu
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ile Gly Asp Gly Gly Val Phe Glu Thr Lys Met
1               5                   10

<210> SEQ ID NO 20
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ile Gly Asp Gly Gly Val Phe Glu Thr Lys Ile
1               5                   10

<210> SEQ ID NO 21
<211> LENGTH: 200
<212> TYPE: PRT
<213> ORGANISM: Homo sapiens

<400> SEQUENCE: 21

Met Ala Phe Thr Glu His Ser Pro Leu Thr Pro His Arg Arg Asp Leu
1               5                   10                  15

Cys Ser Arg Ser Ile Trp Leu Ala Arg Lys Ile Arg Ser Asp Leu Thr
                20                  25                  30

Ala Leu Thr Glu Ser Tyr Val Lys His Gln Gly Leu Asn Lys Asn Ile
            35                  40                  45

Asn Leu Asp Ser Ala Asp Gly Met Pro Val Ala Ser Thr Asp Gln Trp
        50                  55                  60

Ser Glu Leu Thr Glu Ala Glu Arg Leu Gln Glu Asn Leu Gln Ala Tyr
65                  70                  75                  80

Arg Thr Phe His Val Leu Leu Ala Arg Leu Leu Glu Asp Gln Gln Val
                85                  90                  95

His Phe Thr Pro Thr Glu Gly Asp Phe His Gln Ala Ile His Thr Leu
            100                 105                 110

Leu Leu Gln Val Ala Ala Phe Ala Tyr Gln Ile Glu Glu Leu Met Ile
        115                 120                 125

Leu Leu Glu Tyr Lys Ile Pro Arg Asn Glu Ala Asp Gly Met Pro Ile
    130                 135                 140

```
Asn Val Gly Asp Gly Gly Leu Phe Glu Lys Lys Leu Trp Gly Leu Lys
145                 150                 155                 160

Val Leu Gln Glu Leu Ser Gln Trp Thr Val Arg Ser Ile His Asp Leu
            165                 170                 175

Arg Phe Ile Ser Ser His Gln Thr Gly Ile Pro Ala Arg Gly Ser His
        180                 185                 190

Tyr Ile Ala Asn Asn Lys Lys Met
        195                 200

<210> SEQ ID NO 22
<211> LENGTH: 31
<212> TYPE: PRT
<213> ORGANISM: Homo sapiens

<400> SEQUENCE: 22

Asp Tyr Gly Gln Pro Ala Gly Ser Gly Ser Gly Tyr Gly Pro Gln
1               5                   10                  15

Gly Asp Tyr Gly Gln Gln Gly Tyr Gly Pro Gln Gly Ala Pro Thr
            20                  25                  30

<210> SEQ ID NO 23
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Asp Tyr Gly Gln Gln Gly Tyr Gly Pro Gln Gly
1               5                   10

<210> SEQ ID NO 24
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Tyr Gly Pro Gln Gly Asp Tyr Gly Gln Gln Gly
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Asp Tyr Gly Gln Pro Ala Asp Tyr Gly Gln Gln Gly
1               5                   10

<210> SEQ ID NO 26
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26
```

```
Asp Tyr Gly Gln Pro Ala Tyr Gly Pro Gln Gly
1               5                   10

<210> SEQ ID NO 27
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Asp Tyr Gly Gln Gln Gly Tyr Gly Pro Gln Gly
1               5                   10

<210> SEQ ID NO 28
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Tyr Gly Pro Gln Gly Asp Tyr Gly Gln Gln Gly
1               5                   10

<210> SEQ ID NO 29
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Val or Ile
<220> FEATURE:
<221> NAME/KEY: MOD_RES
<222> LOCATION: (3)..(3)
<223> OTHER INFORMATION: Asp or Gln
<220> FEATURE:
<221> NAME/KEY: MOD_RES
<222> LOCATION: (5)..(5)
<223> OTHER INFORMATION: Gly, Ser or Asp
<220> FEATURE:
<221> NAME/KEY: MOD_RES
<222> LOCATION: (6)..(6)
<223> OTHER INFORMATION: Leu, Met, Asp, Val, Arg, Gln, Ile or Thr
<220> FEATURE:
<221> NAME/KEY: MOD_RES
<222> LOCATION: (7)..(7)
<223> OTHER INFORMATION: Phe or Ile
<220> FEATURE:
<221> NAME/KEY: MOD_RES
<222> LOCATION: (8)..(8)
<223> OTHER INFORMATION: Glu, Gln, Thr or Lys
<220> FEATURE:
<221> NAME/KEY: MOD_RES
<222> LOCATION: (9)..(9)
<223> OTHER INFORMATION: Lys, Thr, Gln, Arg or Ala
<220> FEATURE:
<221> NAME/KEY: MOD_RES
<222> LOCATION: (10)..(10)
<223> OTHER INFORMATION: Lys, Arg or Glu
<220> FEATURE:
<221> NAME/KEY: MOD_RES
<222> LOCATION: (11)..(11)
<223> OTHER INFORMATION: Ile, Met, Leu, Phe, Lys, Trp or Tyr

<400> SEQUENCE: 29
```

```
Xaa Gly Xaa Gly Xaa Xaa Xaa Xaa Xaa Xaa Xaa
1               5                   10

<210> SEQ ID NO 30
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 30

His His His His His His
1               5
```